United States Patent [19]
Liang et al.

[11] Patent Number: 6,165,708
[45] Date of Patent: Dec. 26, 2000

[54] ELECTROCHEMILUMINESCENT MONITORING OF COMPOUNDS

[75] Inventors: Pam Liang, Arlington, Va.; Mark T. Martin, Bethesda; Liwen Dong, Rockville, both of Md.

[73] Assignee: IGEN International, Inc., Gaithersburg, Md.

[21] Appl. No.: 08/880,209

[22] Filed: Jun. 23, 1997

Related U.S. Application Data

[63] Continuation of application No. 08/485,419, Jun. 7, 1995, Pat. No. 5,643,713.

[51] Int. Cl.$^7$ ..................................................... C12Q 1/00
[52] U.S. Cl. ............................................. 435/4; 435/7.32
[58] Field of Search ............................. 435/4, 7.32, 7.1, 435/7.2, 18, 29, 34, 39; 549/34

[56] References Cited

U.S. PATENT DOCUMENTS

| | | | |
|---|---|---|---|
| 3,905,871 | 9/1975 | Rubenstein et al. | 435/4 |
| 4,238,195 | 12/1980 | Boguslaski et al. | 435/4 |
| 4,372,745 | 2/1983 | Mandle et al. | 435/4 |
| 4,396,579 | 8/1983 | Schroeder et al. | 435/4 |
| 4,647,532 | 3/1987 | Watanabe et al. | 435/4 |
| 4,725,591 | 2/1988 | Matsuo et al. | 435/4 |
| 4,764,462 | 8/1988 | Bredehorst et al. | 435/4 |
| 4,994,377 | 2/1991 | Nakamura et al. | 435/4 |
| 5,057,302 | 10/1991 | Johnson et al. | 424/1.1 |
| 5,093,238 | 3/1992 | Yamashoji et al. | 435/4 |
| 5,221,605 | 6/1993 | Bard et al. | 435/4 |
| 5,238,610 | 8/1993 | Thompson | 435/4 |
| 5,264,346 | 11/1993 | Chen | 435/4 |
| 5,310,687 | 5/1994 | Bard et al. | 435/4 |
| 5,321,243 | 6/1994 | Sharpless et al. | 435/4 |

OTHER PUBLICATIONS

Blackburn et al; "Electrochemilumescence Detection for Develpoment . . . ", vol. 37(9), Clin. Chem, 1534–1539, 1991.

Vilim and Wilhelm; "What Do We Measure By a Luminol–Dependent Chemiluminescence of Phagocytes?" 6, Free Radical Biology & Medicine, pp. 623–629, 1989.

Allain, C.C. et al; "Enzymatic Determination of Total Serum Cholesterol", vol. 20; Clinical Chemisrty, pp. 470–475, 1974.

Rubenstein and Bard; "Electrogenerated Chemiluminescence", vol. 37, 1981.

*Primary Examiner*—Louise N. Leary
*Attorney, Agent, or Firm*—Whitman Breed Abbott & Morgan LLP

[57] ABSTRACT

Detectable compounds comprising a chemically-transformable first compound covalently linked to an electrochemiluminescent compound are provided. Such compounds are useful in processes and kits that monitor the status of the first compound and derive information from such monitoring.

18 Claims, 17 Drawing Sheets

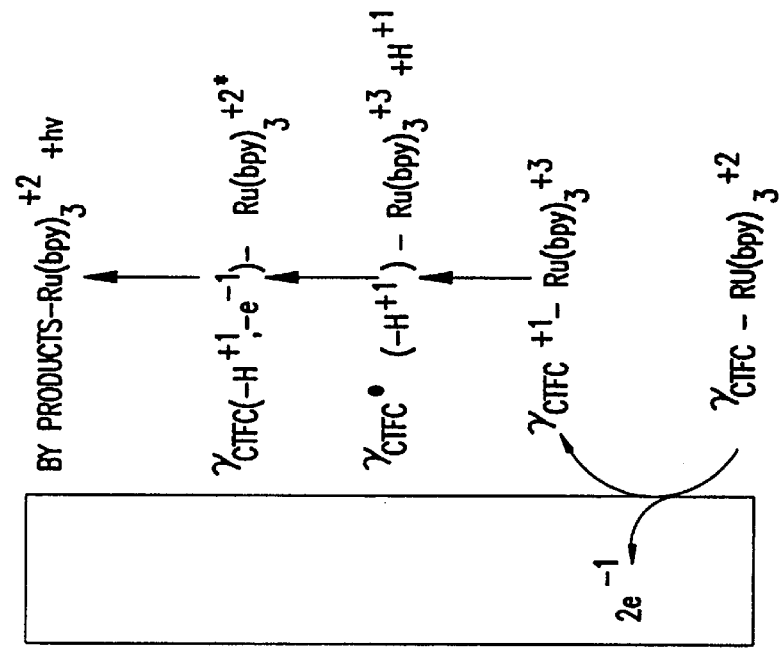
FIG.3b
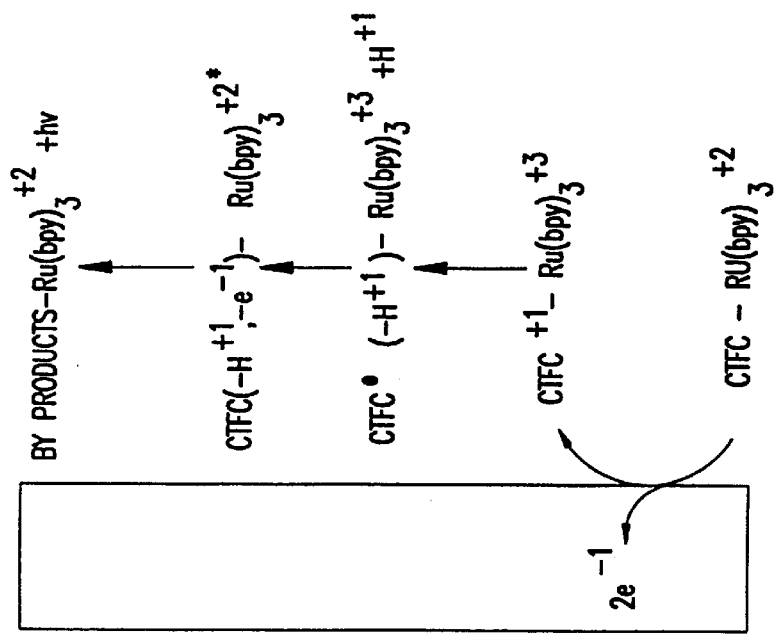
FIG.3a
$$CTFC \xrightarrow{SC} \gamma_{CTFC}$$
FIG.3c

ELECTROCHEMILUMINESCENT MONITORING OF COMPOUNDS

This Appln is a con't of Ser. No. 08/485,419 filed Jun. 7, 1995, U.S. Pat. No. 5,643,713.

FIELD OF THE INVENTION

The present invention is directed generally to analytical biochemistry. More specifically, the present invention is useful for monitoring chemical transformations of detectable compounds having a chemically-tansformable first compound covalently linked to an electrochemiluminescent compound.

BACKGROUND OF THE INVENTION

An ever-expanding field of applications exists for rapid, highly specific, sensitive, and accurate methods of detecting and quantifying chemical, biochemical, and biological substances, including enzymes such as may be found in biological samples. Because the amount of a particular analyte of interest such as an enzyme in a typical biological sample is often quite small, analytical biochemists are engaged in ongoing efforts to improve assay performance characteristics such as sensitivity.

One approach to improving assay sensitivity has involved amplifying the signal produced by a detectable label associated with the analyte of interest. In this regard, luminescent labels are of interest. Such labels are known which can be made to luminesce through photoluminescent, chemiluminescent, or electrochemiluminescent techniques. "Photoluminescence" is the process whereby a material luminesces subsequent to the absorption by that material of light (alternatively termed electromagnetic radiation or emr). Fluorescence and phosphorescence are two different types of photoluminescence. "Chemiluminescent" processes entail the creation of the luminescent species by a chemical reaction. "Electrochemiluminescence" is the process whereby a species luminesces upon the exposure of that species to electrochemical energy in an appropriate surrounding chemical environment.

The signal in each of these three luminescent techniques is capable of very effective amplification (i.e., high gain) through the use of known instruments (e.g., a photomultiplier tube or pmt) which can respond on an individual photon by photon basis. However, the manner in which the luminescent species is generated differs greatly among and between photoluminescent, chemiluminescent, and electrochemiluminescent processes. Moreover, these mechanistic differences account for the substantial advantages as an bioanalytical tool that electrochemiluminescence [hereinafter, sometimes "ECL"] enjoys vis a vis photoluminescence and chemiluminescence. Some of the advantages possible with electrochemiluminescence include: (1) simpler, less expensive instrumentation; (2) stable, nonhazardous labels; and (3) increased assay performance characteristics such as lower detection limits, higher signal to noise ratios, and lower background levels.

As stated above, in the context of bioanalytical chemistry measurement techniques, electrochemiluminescence enjoys significant advantages over both photoluminescence and chemiluminescence. Moreover, certain applications of ECL have been developed and reported in the literature. U.S. Pat. Nos. 5,147,806; 5,068,808; 5,061,445; 5,296,191; 5,247,243; 5,221,605; 5,238,808, and 5,310,687, the disclosures of which are incorporated by reference, detail certain methods, apparatuses, chemical moieties, inventions, and associated advantages of ECL.

Copending and commonly-assigned United States patent application Ser. No. 08/368,429, filed Jan. 4, 1995, the disclosure of which is incorporated by reference, details certain aspects of ECL in connection with beta-lactam and beta-lactamase (neither of which is conjugated through a covalent linkage to an electrochemiluminescent compound).

None of the above-identified documents disclose nor suggest the present invention. Additionally, the practice of the invention offers significant advantages to the skilled bioanalytical chemist in comparison to the electrochemiluminescent techniques taught by these documents. Accordingly, the invention meets the as-yet unmet needs of skilled workers with respect to the achievement of improved assay performance characteristics (e.g., signal output, detection limits, sensitivity, etc.) for the measured species and represents a patentable advance in the field.

SUMMARY OF THE INVENTION

The present invention is directed to compounds, processes, and kits useful for electrochemiluminescent monitoring of compounds. A critical feature of the invention which is common to these compounds, processes, and kits is detectable compounds comprising a chemically-transformable first compound covalently linked to an electrochemiluminescent compound.

In brief, these detectable compounds and their uses represent a patentable advance in the field of electrochemiluminescent measurements because of their attributes. These attributes include the following:

1. They are electrochemiluminescent.;
2. They can be used to monitor chemically-transformable first compounds covalently linked to electrochemiluminescent compounds.; and
3. The above-described monitoring can be extended to become an integral step in performing assays for separate, nonconjugated compounds in sample solutions (e.g., enzymes).

Applicants' present inventions are set forth immediately below in the following nonexclusive, nonlimiting objects of the invention.

A first object of the invention is to provide electrochemiluminescent detectable compounds comprising a chemically-transformable first compound covalently linked to an electrochemiluminescent compound.

A second object of the invention is to provide electrochemiluminescent processes for monitoring chemical transformations of the first compound. Consistent with this second object, assays are provided wherein the chemical transformation of the first compound is an integral step in performing that assay.

A third object of the invention is to provide kits useful for practicing the invention and for implementing the above-described first and second objects of the invention. Consistent with this third object, kits are provided wherein at least one set of solutions containing the detectable compounds is included.

BRIEF DESCRIPTION OF THE DRAWINGS

FIG. 3(a–c) shows a proposed ECL mechanism depicting reaction steps associated with the use of a chemically-transformable first compound as a conjugated reductant.

DETAILED DESCRIPTION OF THE INVENTION

Figure 1:
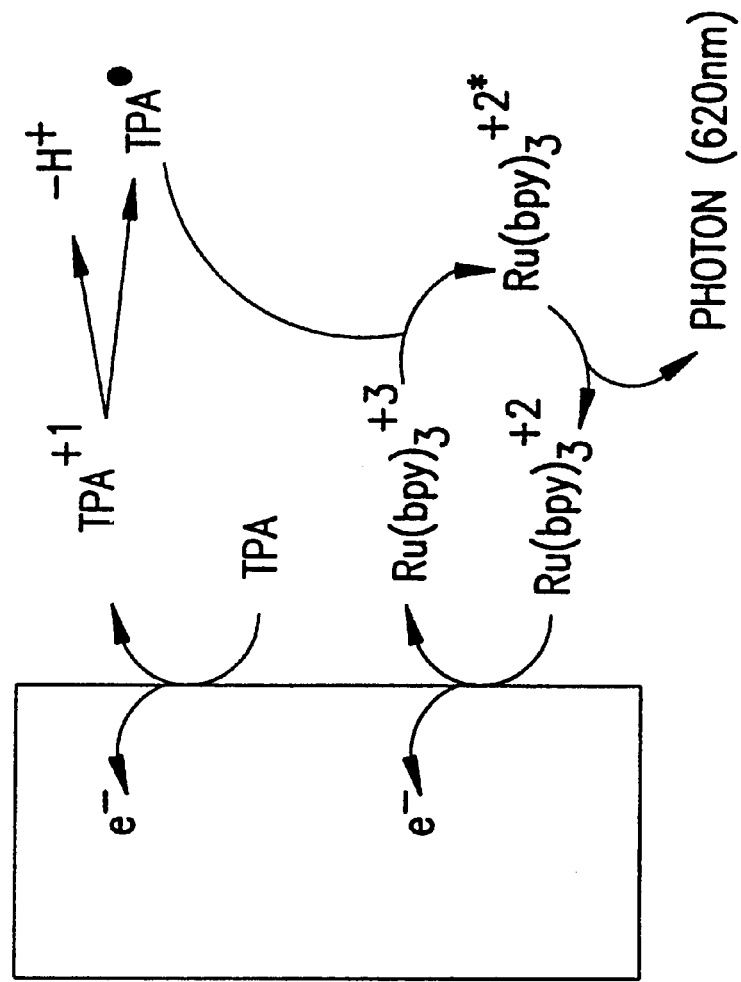
FIG. 1 shows a proposed ECL mechanism depicting reaction steps associated with the use of TPA as a nonconjugated reductant.

The present invention is concerned with detectable compounds comprising (A) a chemically-transformable first compound (B) covalently linked to (C) an electrochemiluminescent compound. The salient features of each of these three portions [(A), (B), and (C)] of the detectable compounds are individually described below. Uses of the detectable compounds appear at (D) while specific examples of the present invention appear at (E).

(A) The Chemically-Transformable First Compounds

The terms "chemically-transformable first compound(s)" (hereinafter "CTFC") and "electrochemiluminescent compound(s)" (hereinafter "EC") each refer to the respective compound independent of certain minor variations of that compound. The skilled worker will understand which minor variation, if any, applies to any particular usage of either CTFC or EC by its context. The following explanations aid in the understanding of this context.

The term CTFC encompasses the following minor variations: (i) certain changes in the formal redox state caused by reduction or oxidation reactions and certain chemical changes to the CTFC that do not destroy the covalent linkage between it and the EC (e.g., the ejection by the CTFC of $H^{+1}$); and (ii) certain chemical transformations (e.g., the hydrolysis of the CTFC) which alter the measurable luminescence of the detectable compound in comparison to the measurable luminescence before any of such chemical transformations have occurred.

In comparing the measurable luminescence of the detectable compound before and after such chemical transformation, several combinations are possible as detailed in the chart below.

| measurable luminescence before | measurable luminescence after | |
|---|---|---|
| none | yes (an increase from zero) | |
| yes | none (a decrease to zero) | |
| yes | yes (an increase from nonzero) | |
| yes | yes (a decrease from nonzero) | |
| yes | yes (no change) | INOPERATIVE |
| none | none | INOPERATIVE |

As depicted in this chart, the measurable luminescence of the detectable compound is altered by the chemical transformation of the CTFC; i.e., the measured luminescence before and after the chemical transformation differ from one another. However, there must be some measurable luminescence either before or after, or both before and after, any such chemical transformation. Thus, the fifth and sixth entries in the above chart do not represent compounds encompassed by the present invention while the first four entries do represent compounds encompassed by the present invention.

FIG. 3(a–c) shows a proposed ECL mechanism depicting reaction steps associated with the use of a CTFC as a conjugated reductant that is covalently linked to an EC. More particularly, the EC is exemplified by the ruthenium (II) tris-bipyridyl cation (hereinafter "$Ru(bpy)_3^{+2}$") throughout FIG. 3(a–c). FIG. 3(a–c) illustrates contemplated minor variations in these two compounds (i.e., in a CTFC and in an EC).

FIG. 3(a) depicts the postulated ECL mechanism for a detectable compound comprising a CTFC covalently linked to an EC. The chart below further explains the depicted reactions.

| Symbol | Definition |
|---|---|
| CTFC | electrochemically unchanged CTFC (starting compound) |
| $CTFC^{*+1}$ | radical, electrochemically oxidized CTFC |
| $CTFC^*(-H^{+1})$ | radical, electrochemically neutral CTFC formed by $H^{+1}$ leaving $CTFC^{+1}$ and able to act as a high-energy reductant in a manner similar to TPA |
| $CTFC(-H^{+1}, -e^{-1})$ | electrochemically neutral, nonradical CTFC formed by $CTFC^*(-H^{+1})$ intramolecularly donating an electron $(e^{-1})$ to the covalently linked EC |
| $Ru(bpy)_3^{+2}$ | nonexcited EC before electrochemical oxidation |
| $Ru(bpy)_3^{+3}$ | nonexcited EC after electrochemical oxidation |
| $Ru(bpy)_3^{+2}$ | excited EC after being intramolecularly reduced by the $CTFC^*(-H^{+1})$ |
| $Ru(bpy)_3^{+2}$ | nonexcited, regenerated EC formed by the emission of light by excited EC |
| hv | light emitted by the excited EC |

FIG. 3(b) shows, relative to FIG. 3(a), all of the analogous reactions to those of FIG. 3(a) with the exception that the symbol $^Y$CTFC is consistently used to represent the resulting chemically-transformed $^Y$CTFC that is produced by the interaction between a CTFC and a second compound (hereinafter "SC").

FIG. 3(c) shows the schematic depiction of the interaction between a CTFC with a SC to form the resulting $^Y$CTFC.

The detectable compound depicted at FIG. 3(a), (b), (c) represents a compound of the present invention that is able to produce measurable luminescence both before and after the chemical transformation of the CTFC. Thus, this compound exemplifies the third and fourth possible combinations of measurable luminescence contained in the previously discussed chart. The depicted reactions are consistent with postulated reaction mechanisms which culminate in measurable luminescence both before and after the CTFC has been chemically transformed. For compounds of the present invention falling within the first and second entries of the previously discussed chart (i.e., for those compound that only produce measurable luminescence either before or (exclusively) after the chemical transformation of the CTFC), only the reaction mechanisms of either FIG. 3(a) or (exclusively) FIG. 3(b) is representative for any particular compound.

With regard to the minor variations of (i), both electrochemical redox reactions and non electrochemical redox reactions are encompassed. Additionally, such changes are integral with and associated with the postulated electrochemiluminescent mechanism including (a) steps leading to the formation of a high-energy reductant as a form of the CTFC; and (b) steps leading to the actual luminescence by the EC.

With regard to the minor variations of (ii), chemical transformations that affect the intramolecular electron-donating ability of the CTFC when it acts as a high-energy reductant in electrochemiluminescence mechanisms are encompassed. The hydrolysis of a CTFC/substrate by either NaOH or an enzyme is an example of such a chemical transformation.

A critical feature of the CTFC is that it remains covalently linked to the EC throughout all of the postulated reactions. Thus, it is understood that the previously discussed changes in and to the CTFC specifically exclude changes which would destroy/break the covalently linkage of the CTFC to the EC. It is also understood that the changes in and to the CTFC alter the intramolecular electron-donating ability of the CTFC so that the measurable luminescence differs before and after any such changes. The CTFC is chosen so that there is measurable luminescence either before or (exclusively) after, or both before and after, any such changes.

Returning to the explanation of the term CTFC and the minor variations encompassed therein, the scope of these variations is clear to the skilled worker.

The CTFC must be able to participate in the ECL mechanisms that cause the EC to luminesce. Specifically, the CTFC must function as a high-energy reductant capable of intramolecularly providing an electron to the EC so the EC is reduced into an excited (i.e., emissive) state. Suitable high-energy reductants for forming the excited state EC often have an unpaired electron and are knows as radicals. FIG. 1 illustrates a proposed ECL mechanisms which uses TPA as a nonconjugated high-energy reductant. This mechanisms generates the actual high-energy reductant in situ subsequent to the initial electrochemical oxidation (triggering) of the TPA precursor. Suitable candidates for the CTFC of the present invention are within the knowledge of the skilled worker based on the disclosure herein.

Applicants are not required to understand the theoretical underpinnings which explain the observed behavior of the detectable compounds. While not wishing to be bound by any particular scientific explanation for these observed properties, applicants postulate the following explanations (I) and (II).

(I.) The ability of the covalently linked CTFC to act as a high-energy reductant by intramolecularly donating an electron to the EC varies according to whether that CTFC has or has not yet undergone a suitable chemical transformation. This variance can, depending upon the particular CTFC involved, either increase or decrease the measured luminescence in any one of the four previously discussed combinations. The chemical transformation in a CTFC resulting from the interaction with a SC appears to cause this variance in intramolecular electron-donating ability because of structural changes in the CTFC which might effect (i) the route through which the reducing electron has to pass through; (ii) the ability of the reducing electron to begin traveling through any such route; or (iii) stereochemical/spatial orientation considerations.

(II.) The ability of the covalently linked CTFC to act as a high-energy reductant by intramolecularly donating an electron to the EC is greater in comparison to the ability of that same (nonconjugated) CTFC to intermolecularly donate an electron to the EC. Correspondingly, the measured luminescence for the detectable compounds of the present invention is greater in comparison with the measured luminescence of electrochemiluminescent compounds where the high energy reductant is not covalently linked to the electrochemiluminescent compound.

Figure 2:
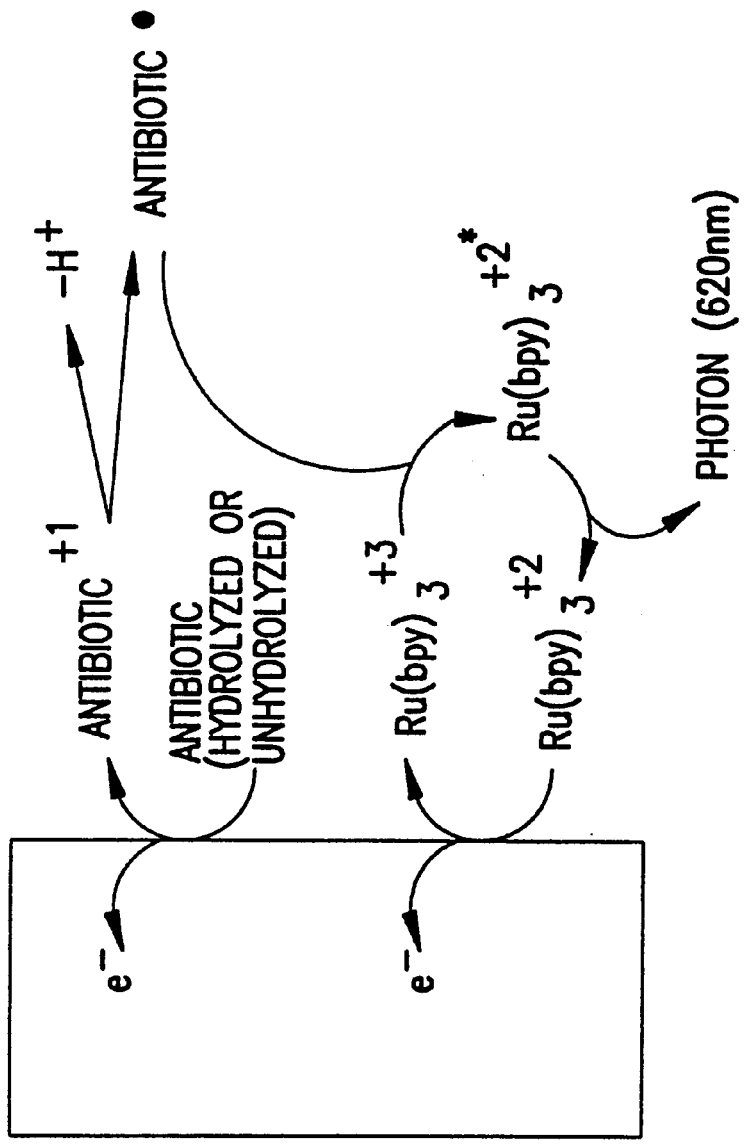
FIG. 2 shows a proposed ECL mechanism depicting reaction steps associated with the use of beta-lactam as a nonconjugated reductant.

Although nonconjugated high energy reductants are not the subject of the present invention; they nicely illustrate the importance of the mechanistic differences. Certain electrochemiluminescent techniques, however, have focused on using such nonconjugated high energy reductants. FIGS. 1 and 2 illustrate proposed electrochemiluminescent mechanisms with such nonconjugated reductants. Specifically, FIG. 1 depicts electrochemiluminescent reactions which use tri-n-propylamine (hereinafter "TPA") as such a reductant while FIG. 2 likewise depicts these reactions with beta-lactam as the reductant. The postulated electrochemiluminescence mechanism shown in FIG. 1 using nonconjugated TPA and Ru(bpy)$_3^{+2}$ has been previously reported in the literature. The postulated electrochemiluminescence mechanisms for beta-lactams (nonconjugated) shown in FIG. 2 [as noted previously, the use of beta-lactams as nonconjugated, high energy reductants in electrochemiluminescence techniques is the subject of a copending and commonly-assigned United States Patent Application] and for the conjugated high energy reductants of the present invention are derived in part from and are thought to be consistent with the mechanistic explanation for the TPA-induced electrochemiluminescence shown in FIG. 1.

Applicants theorize the following explanation as to why, for example, beta-lactam as a nonconjugated reductant generates less electrochemiluminescence than beta-lactam as a conjugated reductant (i.e., as a CTFC). The nonconjugated beta-lactam must first diffuse through solution to become sufficiently proximate to the EC and then intermolecular donate an electron thereto. Moreover, during this diffusion process, the nonconjugated beta-lactam may react with any available species (other than the EC) because it is a very reactive, radical species. In direct contrast, the CTFC does not have to diffuse through the solution as a free species. The CTFC need only intramolecularly donate an electron to the covalently linked EC.

The above analysis teaches attributes of the CTFC sufficiently detailed to enable the skilled worker to practice the present invention. To augment the above teachings, applicants later provide examples using particularly-identified compounds as the CTFC. However, applicants' invention is not limited to any specific compounds; rather applicants' invention is limited only to suitable CTFC as taught by the foregoing.

(B) The Covalent Linkage

The covalent linkage comprises a linker group that covalently links one of the chelating ligands of the EC to the CTFC. Thus, the near end of the linker group terminates with and extends into a covalent bond between an atom of the linker group and an atom of one of the chelating ligands of the EC while the far end of the linker group terminates with and extends into a covalent bond between an atom of the linker group and an atom of the CTFC.

This linker group must have the following attributes to ensure that applicants' detectable compounds are operative. As detailed below, these attributes are divided into two main categories; namely, noninterfering and enhancing.

The noninterfering attributes are properties that the linker group must have because otherwise their presence would interfere with the operability of the invention. Specifically, the linking group during the contemplated practice of the invention must not: (i) prohibit the electrochemical reactions; (ii) prohibit the interactions between the CTFC and the SC; (iii) prohibit the overall electrochemiluminescence mechanism; and (iv) be itself destroyed by the necessary reactions of the invention. For example, a linker group containing an electrochemically oxidizable species having a formal oxidation potential close to that of the central metal cation of the EC would not serve as an effective linking group.

The enhancing attributes of the linker group are those attributes that specifically relate to the ability of the CTFC to intramolecularly transfer an electron to the central metal cation of the EC. These enhancing attributes include the length of the linking group and the nature of the bonds within such length. First, the length of the intervening linker group between the CTFC and the EC must (i) allow and permit the appropriate intramolecular electron transfer to occur; and (ii) not prevent any necessary reaction from occurring due to steric or other considerations.

The term "intramolecular" transfer of an electron from the CTFC to the EC encompasses both transfer though bonds and through space. Such "intramolecular" transfers, however, are limited to transfers between a donating compound (i.e., the CTFC) and a corresponding receiving compound (i.e., the EC) which are covalently linked to each other through the linking group. The covalent linkage portion of the detectable compounds must allow and permit at least one these two types of intramolecular transfer.

For intramolecular transfer through bonds, the linker group must provide sufficient delocalized, conductive electrons (e.g., conjugated $\pi$-systems) to enable the electron to travel through the bonds of the linking group to than reach the central metal cation of the EC.

For intramolecular transfer through space, the linker group must enable the CTFC to approach in relative close proximity the central metal cation of the EC. The linker group should be long enough and stereochemically flexible enough so that the CTFC attached to the far end of the linker group can swing back towards the metal cation and then the electron can intramolecularly transfer through the space then separating the CTFC and the EC. An additional limitation on the appropriate length of the linker group is that it should not be so long that the frequency of the described swinging around effect (which effect is thought to be necessary for intramolecular transfer through space) significantly decreases. In the case of an excessively long linker group, the amount of luminescence produced would be lowered.

For example, a linking group that is not sufficiently long/flexible to enable intramolecular transfer through space and contains only saturated bonds without any delocalized electrons (e.g., alkyl chains) would not be an effective linker group.

There are several advantages that the linker group imparts to the detectable compounds as compared to the electrochemiluminescent compounds that are used with nonconjugated high-energy reductants. The detectable compounds of the present invention avoid the use of any diffusion of free species through solutions. Possible advantages include a more rapid generation of the exited, luminescent-form of the EC and higher signals associated with the more effective intramolecular transfer of applicants' present invention as compared to the intermolecular transfer used with nonconjugated high-energy reductants.

This linkage also ensures that the ratio of the CTFC and the EC is one-to-one. This ratio is unlike that associated with electrochemiluminescent techniques which use TPA nonconjugated beta-lactams as the high-energy reductant. Because of this ratio between the two portion of the detectable compounds of the present invention, applicants are able to qualitatively and quantitatively monitor chemical transformations in the CTFC. Unlike known electrochemiluminescent techniques, the compound monitored is simultaneously (i) covalently linked to the EC and (ii) capable of intramolecularly donating an electron to the EC.

Suitable candidates to be tested as linker groups in the present invention are available to those of ordinary skill in the art. In particular, Vol. 136, Methods in Enzymology, K. Mosbach, Ed., pp. 3–30, Academic Press, NY (1987) discloses a series of "spacer molecules" for immobilized active coenzymes, including NAD and ATP. The spacer molecules of this article, which article is fully incorporated by reference, are examples of such suitable candidates.

The above analysis, in connection with the disclosure herein, teaches attributes of the covalent linkage sufficiently detailed to enable the skilled worker to practice the present invention. Thus, the skilled worker can select appropriate candidates as linking groups and determine, by routine experimentation, those which do and do not work. To augment the above teachings, applicants later provide examples using specific detectable compounds having identified linker groups. However, applicants' invention is not limited to any such exemplified linker group. Rather, the present invention is limited only to covalent linkages as taught herein to the skilled worker.

(C) The Electrochemiluminescent Compounds

The third and final portion of the detectable compounds are EC. These and their applications in certain contexts have been reported in the literature. See, for example, the issued U.S. Patents previously incorporated by reference. The attributes and identities of such known EC are known to skilled workers and need not be repeated in detail here.

Thus, the term electrochemiluminescent compound is a term of art whose metes and bounds are known to skilled workers. Nonlimiting, nonexclusive examples of particular detectable compounds (including the EC portion) and their uses are later provided.

The present invention, however, is not directed to EC in and of themselves nor is it directed to any of their known applications. The invention is directed to a novel and nonobvious use of EC; namely, their use in detectable compounds comprising a CTFC covalently linked to an EC. Accordingly, the skilled worker can practice the present invention in accordance with the disclosure herein in combination with the existing knowledge of EC. Notwithstanding this, applicants provide guidelines for providing EC operative in the present invention.

The minor variations encompassed by the term CTFC discussed earlier at (A) apply in an analogous manner to those for the term EC and need not be reexamined here. Thus, changes in formal redox state of the EC due to, for example, electrochemical oxidation and intramolecular reduction as well as excited/nonexcited states are encompassed by the term EC and such changes represent acceptably differing forms of the EC.

The following formula (I.) depicts suitable electrochemiluminescent compounds for use in the present invention:

(I.);

wherein

M is a central metal cation comprising ruthenium or osmium;

$L^1$ through $L^6$ are each ligands of M, each of which may be monodentate or polydentate, and each of which may be the same or different from each other;

a through e are each 0 or 1;

provided that the ligands of M are of such number and composition that the compound can be induced to electrochemiluminescence; and further provided that the total number of bonds provided by the ligands to the central metal cation M equals the coordination number of M.

In the practice of the present invention, preferred electrochemiluminescent compounds include those wherein the central metal cation is ruthenium Ru or osmium Os. A particularly preferred compound is $Ru(bpy)_3^{+2}$.

Having established (i) that electrochemiluminescent compound is a term of art; (ii) guidelines for providing such EC; the term EC as used herein is clear to skilled workers. Nonetheless, applicants later amplify this teaching by providing nonlimiting, nonexclusive particular examples which identify the EC.

(D) Uses of the Detectable Compounds

The identities, attributes, and theoretical basis of the detectable compounds of the present invention have previously been detailed. Consequently, this section details the uses of such detectable compounds.

The electrochemiluminescent processes that use the detectable compounds can be viewed as being divided into two main categories; namely, monitoring and assaying.

The detectable compounds can be used to monitor chemical transformations in the CTFC that alter the effective intramolecular donating ability of that CTFC. These monitoring processes are not primarily designed to qualitatively nor quantitatively identify the presence/amount of any particular SC. Rather, the monitoring processes are designed to qualitatively and/or quantitatively indicate the presence/extent of chemical transformations in the CTFC without requiring identifications directed to which particular SC in the sample solution is responsible for any such chemical transformations.

By comparing (i) the measured luminescence of the detectable compound after the exposure of that detectable compound to sample solutions suspected of containing at least one SC that is capable of interacting with the CTFC and of effecting a chemical transformation in the CTFC with (ii) the measured luminescence of the predetermined standard, the CTFC is effectively monitored. More specifically, the presence and extent of such chemical transformations in the CTFC can be monitored. The predetermined luminescence standard of the monitoring process is generated in the following manner.

The preparation of this calibration curve is illustrated for a detectable compound able to produce measurable luminescence before any chemical transformations in the CTFC. Known differing amounts of a particular detectable compound are (in the purposeful absence of any SC capable of interacting with the CTFC to cause a chemical transformation) prepared in a series of sample solutions. Each of these sample solutions is caused to electrochemiluminescence upon exposure to electrochemical energy in the form of a positive voltage bias imposed on an electrode of an electrochemiluminescent cell. The resulting experimentally measured luminescence is recorded. The predetermined luminescence standard for monitoring techniques comprises a calibration curve having experimentally measured luminescence on a first axis and known amounts of the particular detectable compound on the second axis. By comparing the experimentally measured luminescence of a solution containing a known quantity of the detectable compound and also containing a sample suspected of containing any second compounds with the corresponding luminescence value from the calibration curve, the CTFC is effectively monitored. Changes in the CTFC caused by interactions with any second compounds in the sample solution will result in measurable differences (deviations) from the calibration curve.

The monitoring processes can be used to screen suspected solutions for activity against the CTFC. Specifically, a series of sample solutions could be monitored with the detectable compounds. A positive electrochemiluminescence test result (i.e., a result that is either higher or lower than the predetermined standard) for any particular sample solution is indicative of at least one SC in that particular sample solution. Accordingly, that solution would then be an appropriate candidate for further detailed investigations.

The assaying processes are extensions of the monitoring processes in that the assaying processes are designed to specifically test for the presence and/or amount of a particular SC. As such, the assaying processes likewise are based on the chemical transformations in the CTFC which alter the effective intramolecular donating ability of the CTFC to the EC.

By comparing (i) the measured luminescence of the detectable compound after the exposure of that detectable compound to a sample solution suspected of containing a particular SC that is capable of interacting with the CTFC and of effecting a chemical transformation in the CTFC with (ii) the measured luminescence of the predetermined standard, the particular SC is effectively assayed. More specifically, the presence and amount of the particular SC can be assayed. The predetermined luminescence standard of the assaying process is generated in the following manner.

Known amounts of a particular detectable compound are exposed to a series of sample solutions each containing known differing amounts of a particular SC that is capable of interacting with the CTFC of the detectable compound in accordance with the present invention. The exposure is effected under conditions favorable to and consistent with the desired interactions. Subsequent to such interactions, each of these sample solutions is caused to electrochemiluminescence and the experimentally measured luminescence is recorded. The predetermined luminescence standard for assaying processes comprises a calibration curve having experimentally measured luminescence on a first axis and known amounts of the particular SC on the second axis.

For both monitoring and assaying processes, the experimentally measured luminescence may be either greater than or less than the luminescence for the applicable predetermined luminescence calibration curve. In other words, the interaction between the CTFC and the at least one second compound may either increase or decrease the effective intramolecular electron donating ability of that CTFC (which would correspondingly increase or decrease the experimentally measured luminescence).

Preferred applications of the detectable compounds are monitoring and assaying processes when the CTFC first compound comprises a substrate and the SC comprises an enzyme that is specific to that substrate. Particularly preferred substrates are beta-lactams. Such beta-lactams are useful in assaying processes that test for the corresponding beta-lactamase.

Another application of the detectable compounds of the present invention takes advantages of coupled, regenerative reaction mechanism that involve the conversion of a separate, nonconjugated substrate in solution into a separate, nonconjugated product in solution via exposure to an appropriate enzyme and co-mediators. The interactions between the CTFC and the enzyme-catalyzed, co-mediated conversion of a substrate species in solution to a product species in solution forms the theoretical underpinnings for an assay that can be specific to the substrate in solution, the enzyme in solution, and/or the CTFC.

Another use of the detectable compounds of the invention are in kits specifically designed to implement the processes of the present invention. Accordingly two types of kits are provided. The monitoring kits each comprise a plurality of sample standard solutions each containing known amounts of a particular detectable compound with the purposeful absence of any SC. These monitoring kits can be used to determine the predetermined luminescence standard calibration curve. The assaying kits each comprise a plurality of sample solutions each containing known amounts of a particular detectable compound in addition to a corresponding plurality of test solutions each containing known differing amounts of a particular SC that is capable of interacting with the detectable compound in the described manner.

(E) EXAMPLES

Notwithstanding the previous detailed description of the present invention, applicants below provide specific examples solely for purposes of illustration and as an aid to understanding the invention. Particularly with respect to the protection to which the present invention is entitled to, these examples are both nonlimiting and nonexclusive. Accordingly, the scope of applicants' invention as set forth in the appended claims is to be determined in light of the teachings of the entire specification without incorporating in such claims the specific limitations of any particular example.

Example 1

Figure 4:
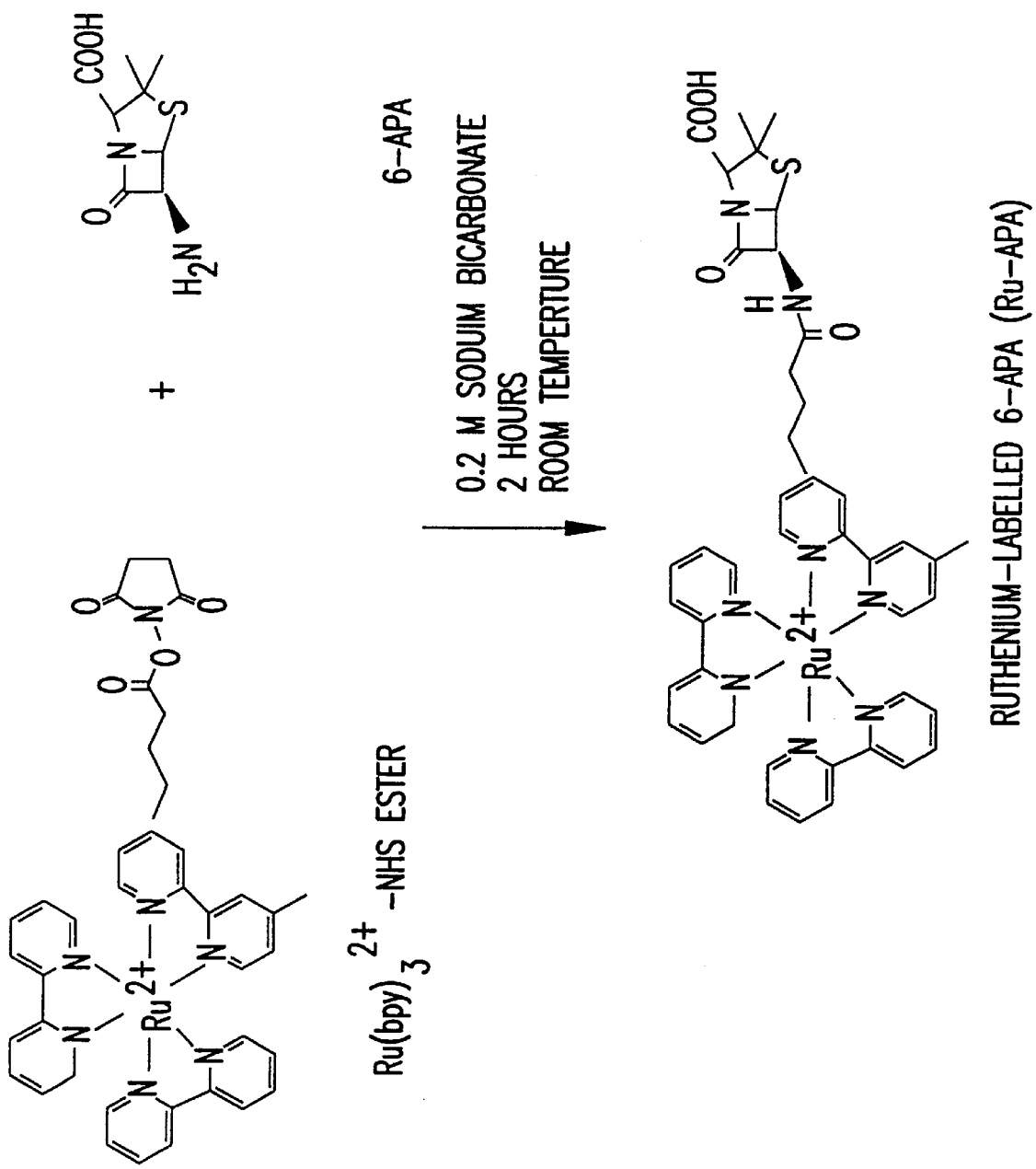
FIG. 4 shows the synthesis of Ru-AMP.
Figure 5:
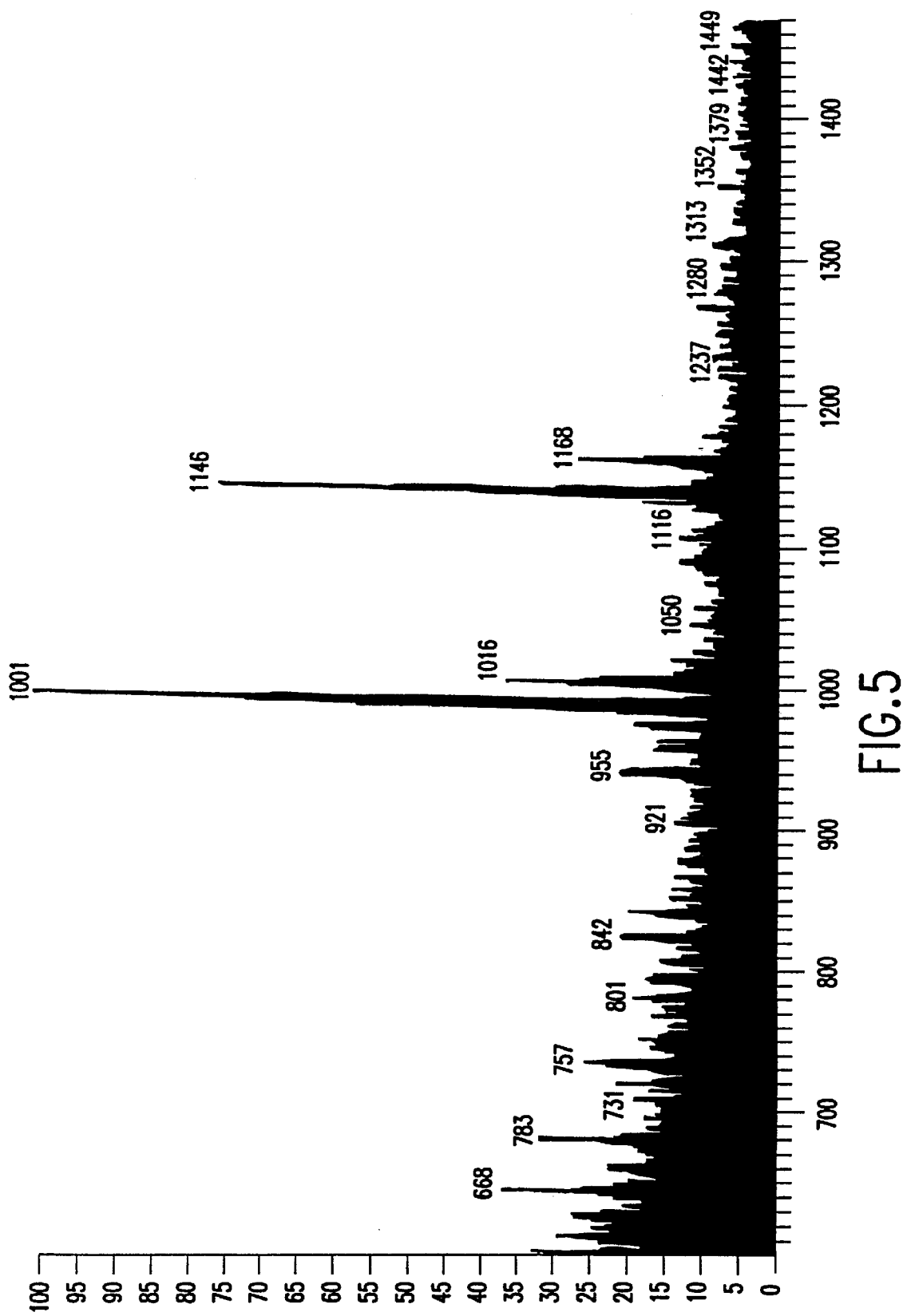
FIG. 5 shows the mass spectrum of the ammonium hexafluorophosphate salt of Ru-AMP.
Figure 6:
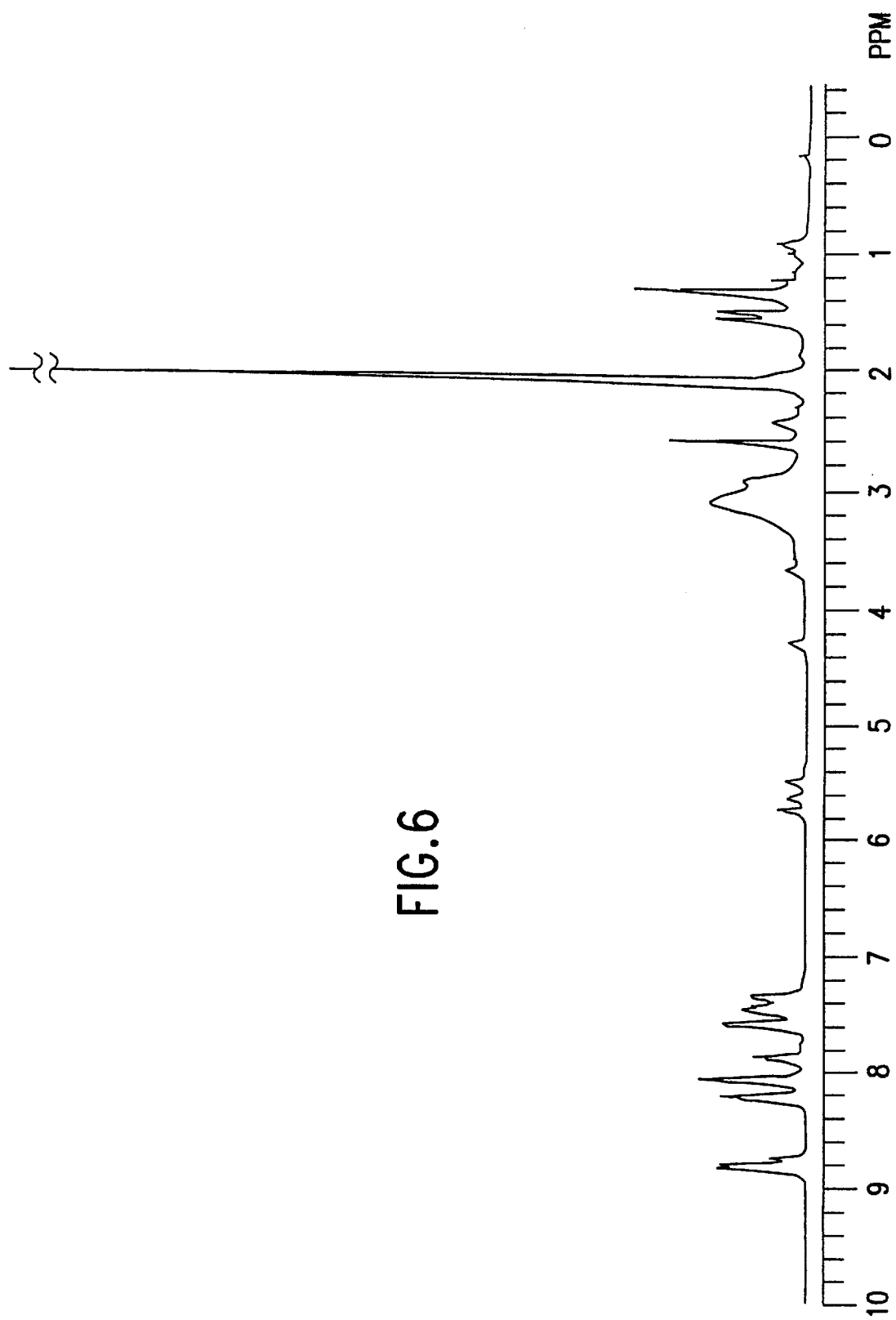
FIG. 6 shows the proton NMR spectrum of the ammonium hexafluorophosphate salt of Ru-AMP.

Preparation of $Ru(bpy)_3^{+2}$-Labeled Beta-Lactam Antibiotics (a) Preparation of $Ru(bpy)_3^{+2}$-labeled ampicillin (Ru-AMP):

$Ru(bpy)_3^{+2}$-NHS ester (15.1) mg in acetonitrile (250 μL) was mixed with ampicillin (29.1 mg) in 0.2 M sodium bicarbonate, pH 8.0 (250 μL) and the reaction was allowed to proceed at room temperature for 2 hours (FIG. 4). Ru-AMP was purified using a Waters HPLC system (Milford, Mass.) equipped with a Progel™-TSJ CM-5PW column (7.5 cm×7.5 mm) (Supelco, Inc., Bellefonte, Pa.) using a 1.0 mL/minute, 15-minute linear gradient from 20–180 mM sodium phosphate, pH 7.0. Substrate was quantitated spectrophotometrically by measuring the absorbance of the ruthenium complex (the molar extinction coefficient at 453 nm is 13,700 $M^{-1}$ $cm^{-1}$). Following formation of the ammonium hexafluorophosphate salt, the structure and purity of Ru-AMP was confirmed by mass spectroscopy and proton NMR (FIGS. 5–6).

(b) Preparation of $Ru(bpy)_3^{+2}$-labeled 6-aminopenicillanic acid (hereinafter "Ru-APA")

Figure 7:
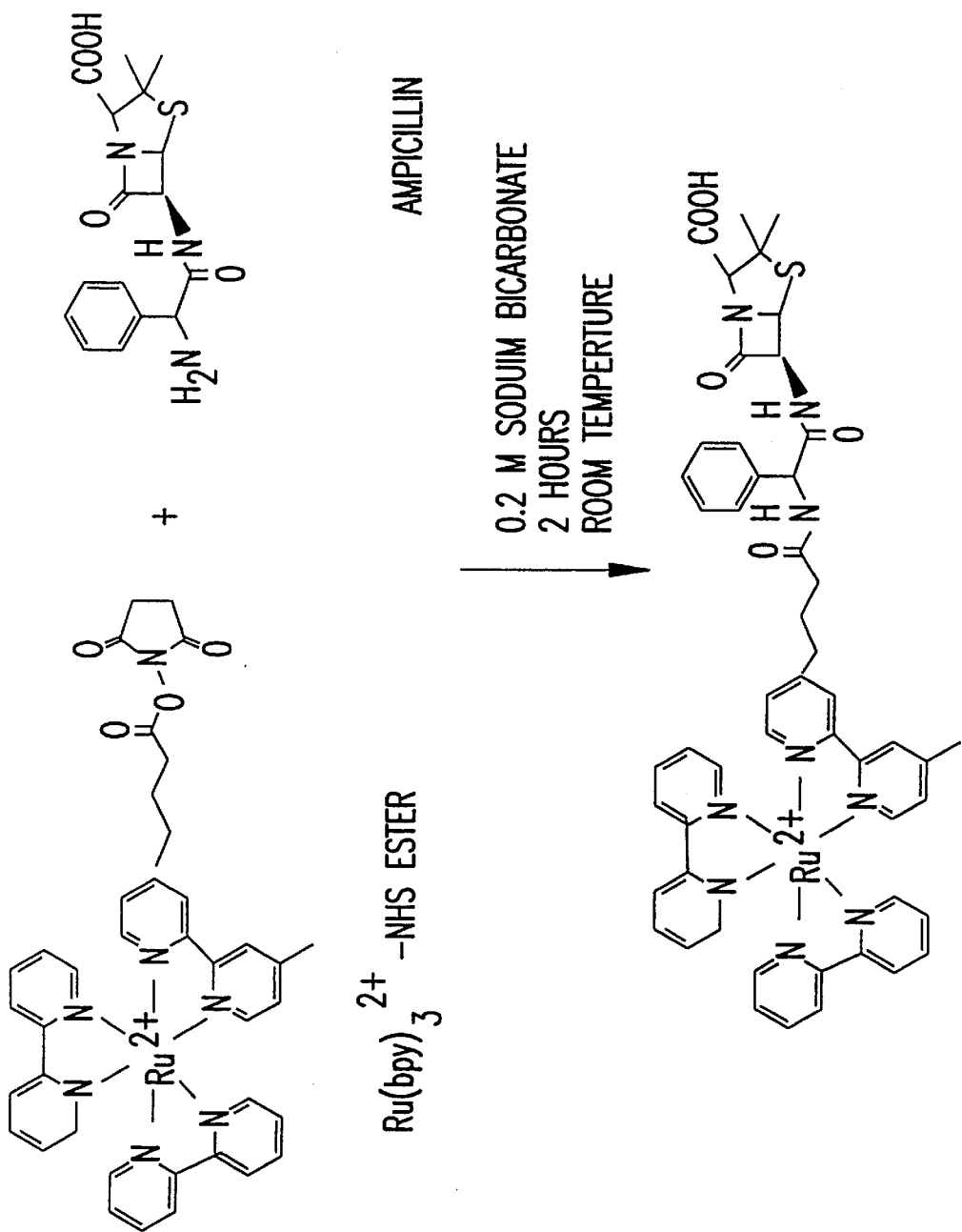
FIG. 7 shows the synthesis of Ru-APA.

$Ru(bpy)_3^{+2}$-NHS ester (15 mg) (IGEN, Inc., Gaithersburg, Md.) in acetonitrile (250 μL) was mixed with 6-aminopenicillanic acid (12.4 mg) in 0.2 M sodium bicarbonate, pH 8.0 (350 μL) and the reaction was allowed to proceed at room temperature for 2 hours (FIG. 7). Ru-APA was purified with a Waters HPLC system (Milford, Mass.) equipped with a Progel™-TSK CM-5PW column (7.5 cm×7.5 mm) (Supelco, Inc., Bellefonte, Pa.) using a 1.0 mL/minute, 20-minute linear gradient from 20–100 mM sodium phosphate, pH 7.0. Substrate was quantitated spectrophotometrically by measuring the absorbance of the ruthenium complex (the molar extinction coefficient at 453 nm is 13,700 $M^{-1}cm^{-1}$).

(c.) Preparation of other $Ru(bpy)_3^{+2}$-labeled beta-lactams

Figure 8:
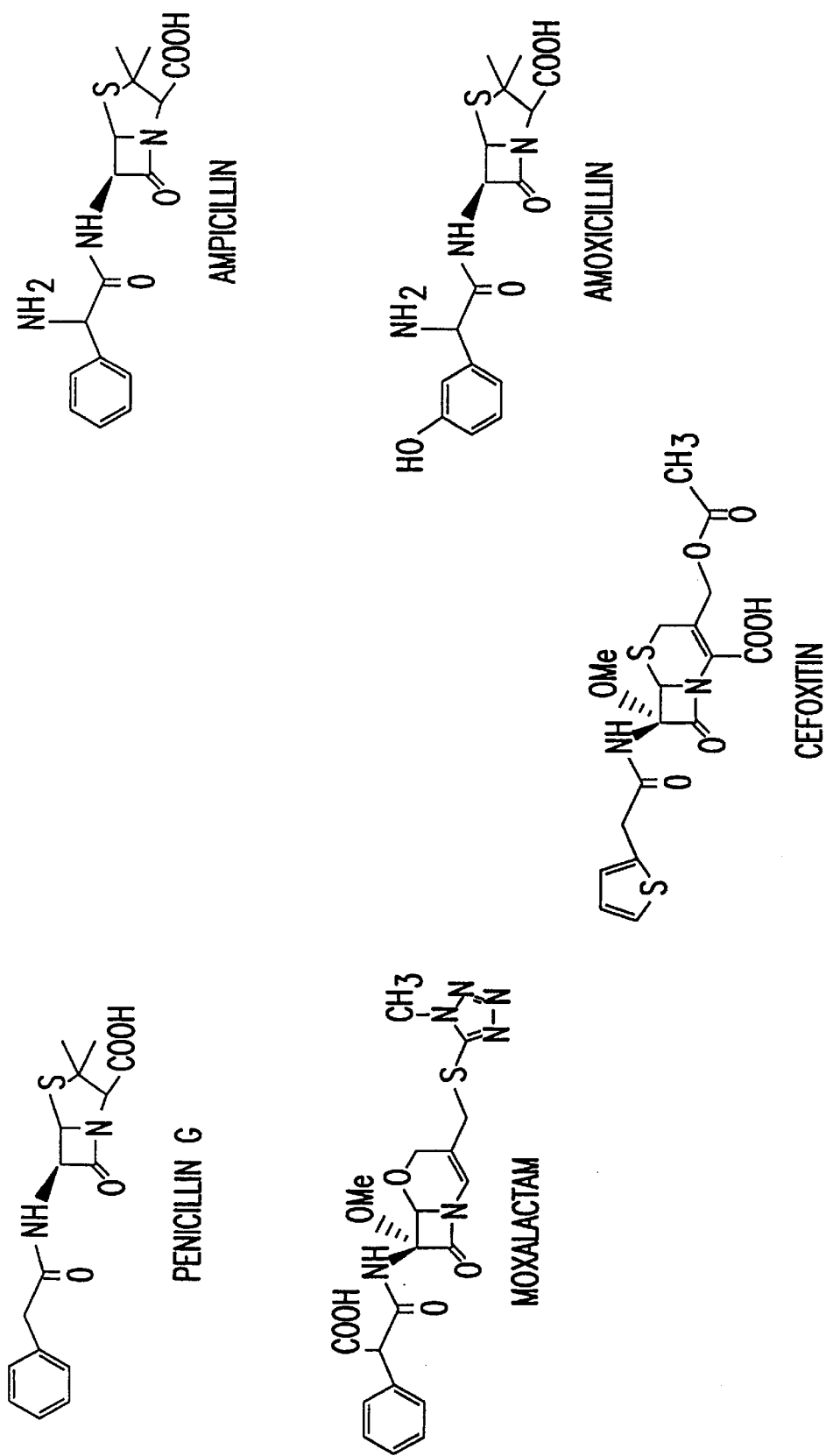
FIG. 8 shows the structures of 5 specific beta-lactams.

Other beta-lactams, such as 7-aminocephalosporanic acid, that have a primary amine in their structures can also react with $Ru(bpy)_3^{+2}$-NHS ester to form similar conjugates as described above. The reaction and purification conditions will be similar, potentially differing somewhat in ways solvable by one skilled in the art. FIG. 8 shows the structure of 5 specific beta-lactams.

Example 2

ECL Assay of Ru-AMP Hydrolysis

Figure 9:
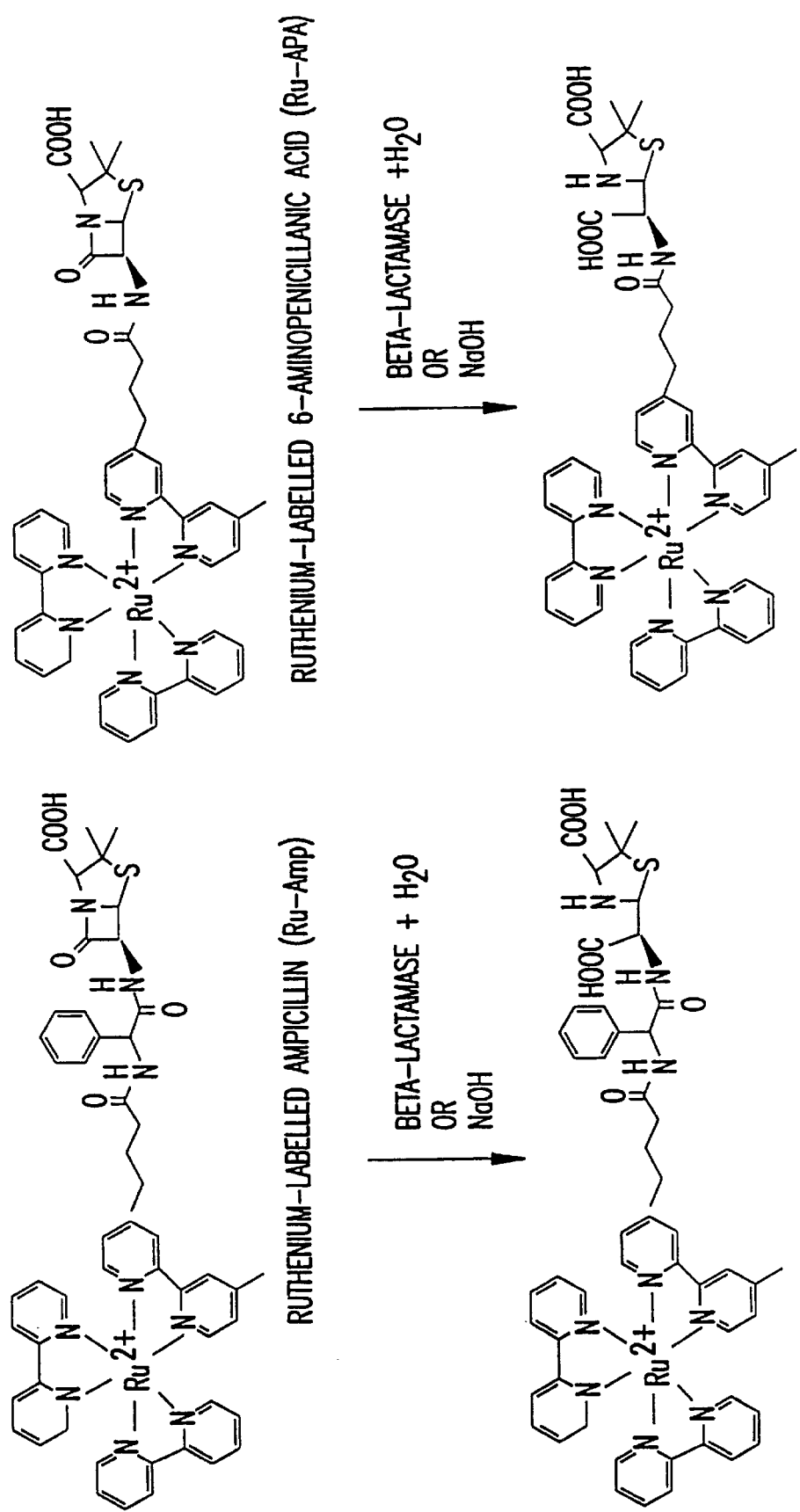
FIG. 9 shows the hydrolysis by NaOH or by beta-lactamase enzyme of Ru-AMP (left side) and of Ru-APA (right side).

Experiments were performed to compare the ECL properties of Ru-AMP (conjugated) with $Ru(bpy)_3^{+2}$ and ampicillin mixtures (nonconjugated). ECL properties were compared both before and after NaOH and enzymatic hydrolysis (FIG. 9, left side).

Ru-AMP was found to be a very good substrate of beta-lactamase. Hydrolysis of Ru-AMP (33 μM) by beta-lactamase I from *Bacillus cereus* (0.3 nM) was monitored spectrophotometrically at 240 nm using a Hitachi U3200 spectrophotometer (Danbury, Conn.) at 25.0° C. in 0.1 M sodium phosphate, pH 7.0. Half-time ($t_{1/2}$) analysis gave a $k_{cat}/K_m$ for enzymatic hydrolysis of Ru-AMP of $3.9 \times 10^8$ $min^{-1}M^{-1}$.

Figure 10:
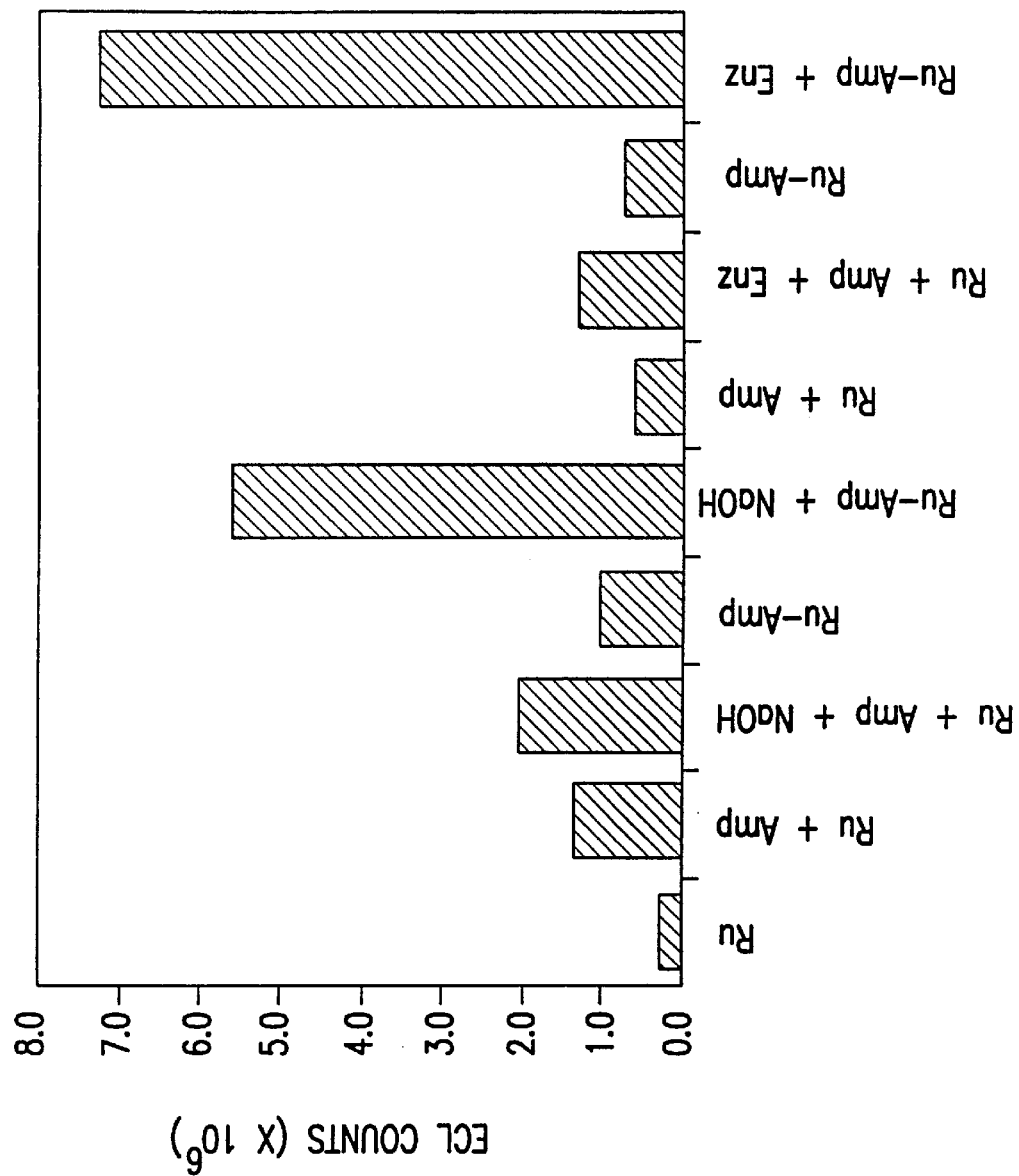
FIG. 10 shows the comparison of measured ECL for a series of different samples.

The ECL properties of equimolar mixtures of Ru(bpy)$_3^{+2}$ and ampicillin (hydrolyzed or unhydrolyzed) were compared to the same concentration of the Ru-AMP conjugate (hydrolyzed or unhydrolyzed). In separate experiments, ampicillin and Ru-AMP were hydrolyzed by either 250 mM NaOH (base hydrolysis) or 441 nM beta-lactam I from *Bacillus cereus* (enzyme hydrolysis). For base hydrolysis, 50 μL of 5 M NaOH were added to 1.0 mL solutions of deionized water containing either 24.85 μM Ru-AMP or a mixture of 25 μM ampicillin and 25 μM Ru(bpy)$_3^{+2}$. Following 30 minute incubations, the solutions were neutralized with 50 μL of 5 M HCl. For the unhydrolyzed counterpart experiments, 50 μL of H$_2$O were added to solutions of either 24.85 μM Ru-AMP or a mixture containing 25 μM ampicillin and 25 μM Ru(bpy)$_3^{+2}$. Following 30 minute incubations, 50 μL of 5 M NaCl was added to these solutions. The results shown in FIG. 10 demonstrate: (1) that ampicillin hydrolysis by either NaOH or beta-lactamase causes an increase in the ECL of the mixtures; and (2) that the increase in the ECL caused by the hydrolysis is dramatically greater when the light-emitting ruthenium complex is covalently linked to ampicillin. With base hydrolysis, ECL increased 1.5-fold when ampicillin was hydrolyzed in a mixture of ampicillin and Ru(bpy)$_3^{+2}$, while ECL increased 5.2-fold when Ru-AMP was hydrolyzed. Similar results were obtained in enzyme hydrolysis: ECL increased 2.1-fold when ampicillin was hydrolyzed in a mixture of ampicillin and Ru(bpy)$_3^{+2}$, while ECL increased 9.8-fold upon hydrolysis of Ru-AMP. The data establishing these conclusions is found in FIG. 10 which shows the experimentally measured electrochemiluminescence of (from left to right):

Ru(bpy)$_3^{+2}$ alone;
Ru(bpy)$_3^{+2}$ plus unhydrolyzed ampicillin;
Ru(bpy)$_3^{+2}$ plus NaOH-hydrolyzed ampicillin;
unhydrolyzed Ru-AMP;
NaOH-hydrolyzed Ru-AMP;
Ru(bpy)$_3^{+2}$ plus unhydrolyzed ampicillin;
Ru(bpy)$_3^{+2}$ plus beta-lactamase-hydrolyzed ampicillin;
unhydrolyzed Ru-AMP; and
beta-lactamase-hydrolyzed Ru-AMP.

Figure 11:
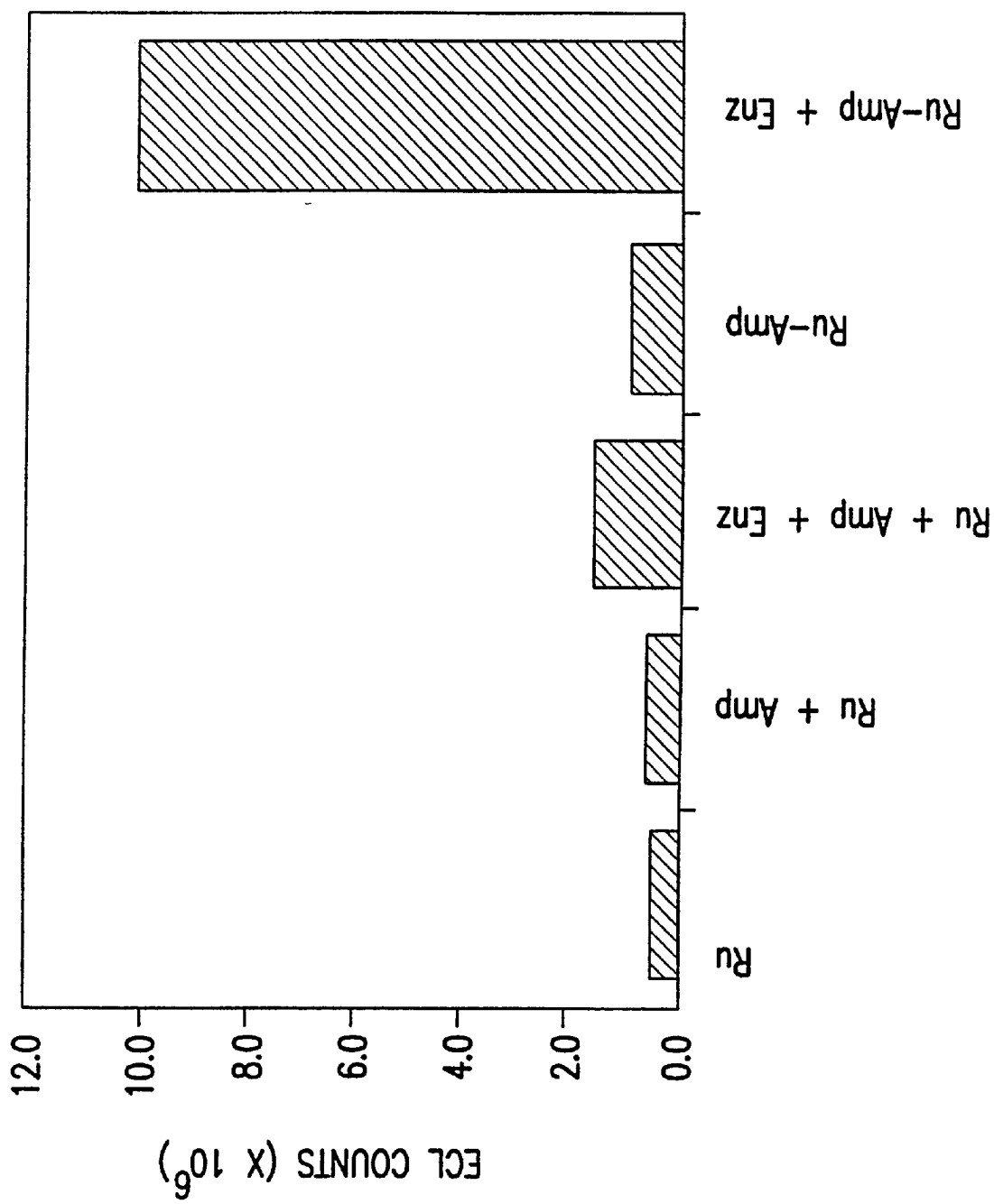
FIG. 11 shows the comparison of measured ECL for a series of different samples.

This work was confirmed in a second experiment using enzyme hydrolysis which differed in that the incubation time with enzyme was lengthened from 30 to 60 minutes (FIG. 11). Here, enzyme hydrolysis caused a 2.5-fold increase in ECL when ampicillin and Ru(bpy)$_3^{+2}$ were unconjugated and an 11.1-fold increase in ECL when the Ru-AMP conjugate was hydrolyzed. The data establishing these conclusions is found in FIG. 11 which shows the experimentally measured luminescence of (from left to right):

Ru(bpy)$_3^{+2}$ alone;
Ru(bpy)$_3^{+2}$ plus unhydrolyzed ampicillin;
Ru(bpy)$_3^{+2}$ plus beta-lactamase-hydrolyzed ampicillin;
unhydrolyzed Ru-AMP; and
beta-lactamase-hydrolyzed Ru-AMP.

These results show that Ru(bpy)$_3^{+2}$-conjugation caused intramolecular effects that dramatically increase the experimentally measured luminescence when the beta-lactam ring is hydrolyzed.

Figure 12:
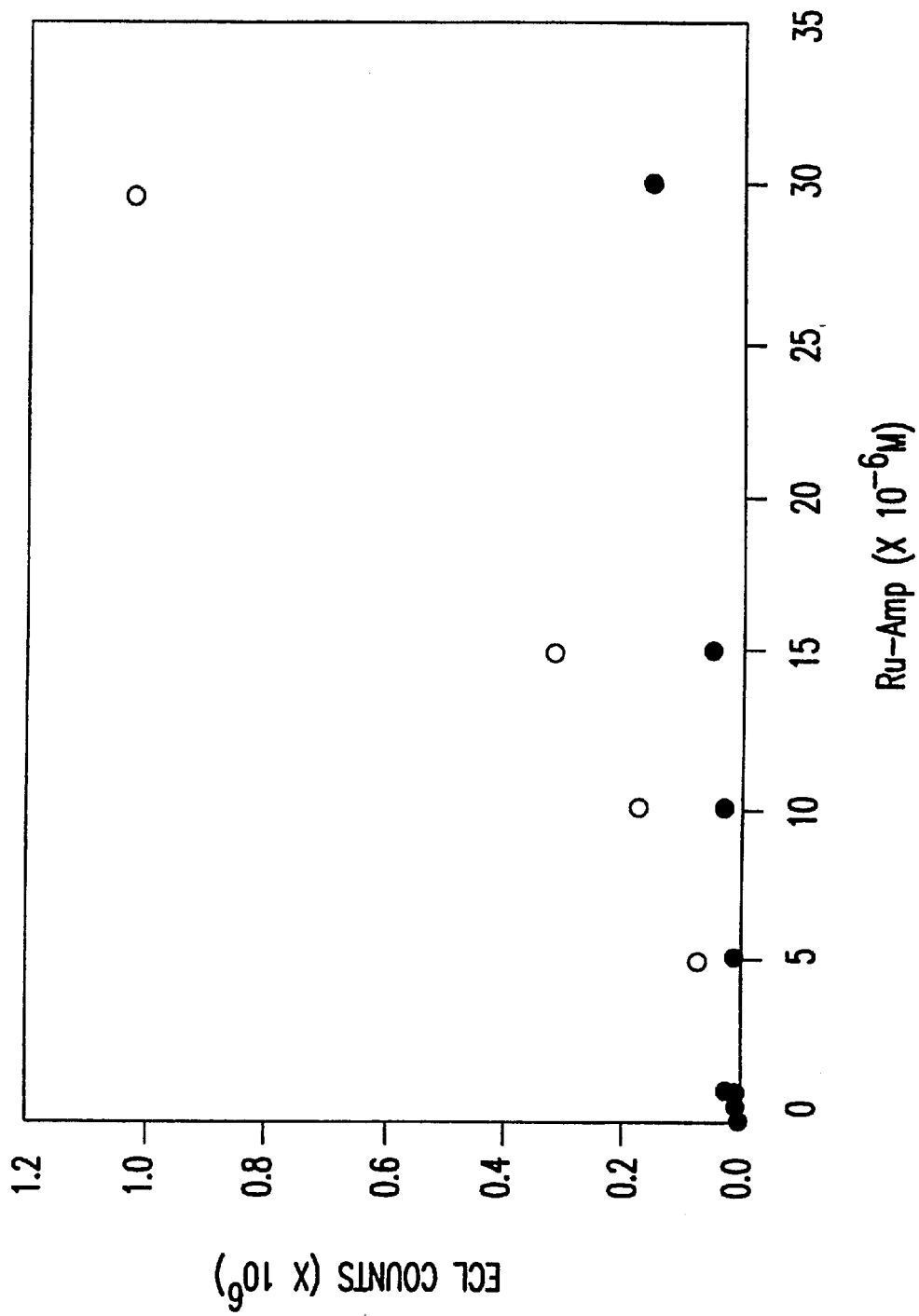
FIG. 12 shows the effect of unhydrolyzed (closed circles) and hydrolyzed (open circles) Ru-AMP concentration on the measured ECL.

FIG. 12 shows that low concentrations of Ru-AMP can be detected by hydrolysis. The lower limit of detection was found to be 50 nM (464 relative ECL counts for hydrolyzed Ru-AMP versus an average instrument reading of –152 relative counts for unhydrolyzed Ru-AMP). This compares favorable to the lower limit for detection of (unconjugated) ampicillin hydrolysis which was 5000 nM.

Example 3

ECL Assay of Ru-APA Hydrolysis

It was thought that Ru-APA might have different ECL properties (before and after hydrolysis) from those of Ru-AMP. The differences would be a consequence of the structural differences between APA and AMP, especially the difference in distance between the beta-lactam ring and the primary amino group used to conjugate Ru(bpy)$_3^{+2}$-NHS ester (FIG. 9, right side). In Ru-AMP, the beta-lactam ring is three bond lengths farther from the amino group than in Ru-APA. Specifically, hydrolysis of Ru-APA (or other beta-lactam conjugates) may be more or less sensitively detected by ECL than Ru-AMP hydrolysis.

The ECL properties of the Ru-APA conjugate were compared with those of the mixtures of unconjugated Ru(bpy)$_3^{+2}$ and 6-APA. ECL properties were compared before and after NaOH and enzymatic hydrolysis. The data was then compared to the results of similar experiments with Ru-AMP described in Example 2.

Ru-APA was found to be a very good substrate of beta-lactamase. Hydrolysis of Ru-APA (23 μM) by beta-lactamase I from *Bacillus cereus* (0.6 nM) was monitored spectrophotometrically at 240 μm using a Hitachi U3200 spectrophotometer (Danbury, Conn.) at 25.0° C. in 0.1 M sodium phosphate, pH 7.0. Half-time ($t_{1/2}$) analysis gave a $k_{cat}/K_m$ for enzymatic hydrolysis of Ru-APA of 9.8×10$^7$ min$^{-1}$M$^{-1}$. This rate indicates that the enzyme hydrolyzed Ru-APA with a 4-fold lower efficiency than Ru-AMP, but that Ru-APA hydrolysis by beta-lactamase is still exceptionally efficient.

The ECL properties of equimolar mixtures of Ru(bpy)$_3^{+2}$ and APA (hydrolyzed or unhydrolyzed) were compared with the same concentration of the Ru-APA conjugate (hydrolyzed or unhydrolyzed). In separate experiments, 6-APA and Ru-APA were hydrolyzed by either 250 mM NaOH (base hydrolysis) or 347 nM beta-lactamase I from *Bacillus cereus* (enzyme hydrolysis).

Figure 13:
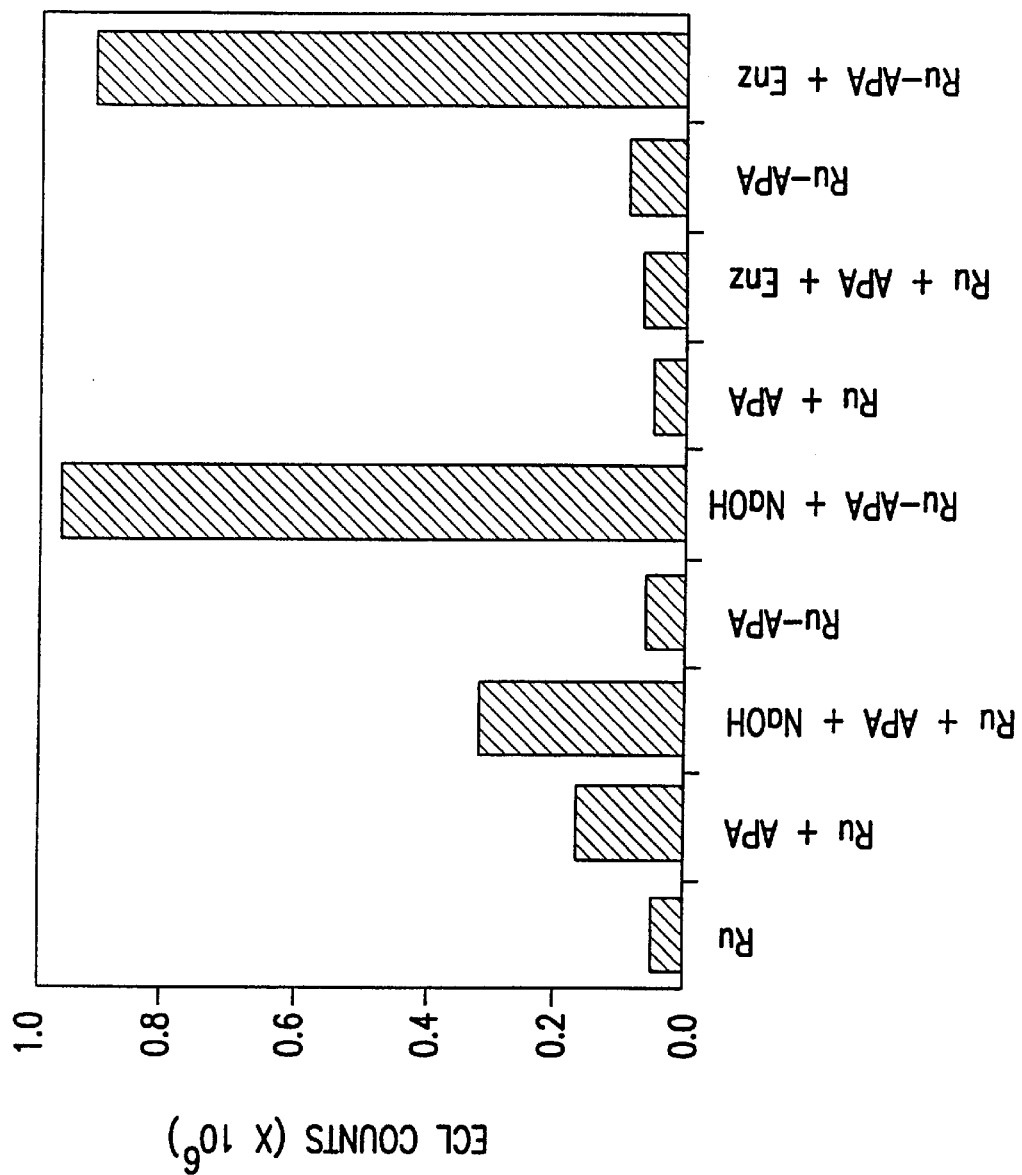
FIG. 13 shows the comparison of measured ECL for a series of different samples.

For base hydrolysis, 50 μL of 5 M NaOH were added to 1.0 mL solutions of deionized water containing either 23.0 μM Ru-APA or a mixture containing 23.0 μM APA and 23.0 μM Ru(bpy)$_3^{+2}$. Following 60 minute incubations, the solutions were neutralized with 50 μL of 5 M HCl. For unhydrolyzed counterpart experiments, 50 μL of H$_2$O were added to solutions of either 23.0 μM Ru-APA or a mixture of 23.0 μM APA and 23.0 μM Ru(bpy)$_3^{+2}$. Following 60-minute incubations, 50 μL of 5 M NaCl was added to these solutions. The results shown in FIG. 13 demonstrate: (1) that 6-APA (conjugated or nonconjugated) hydrolysis by either NaOH or beta-lactamase causes an increase in ECL; and (2) that the increase in ECL caused by hydrolysis is dramatically greater when the light-emitting ruthenium complex is covalently coupled to 6-APA. With base hydrolysis, ECL increased 1.9-fold when 6-APA (nonconjugated) in a mixture of 6-APA and Ru(bpy)$_3^{+2}$ was hydrolyzed, while ECL increased 13.2-fold when Ru-APA (conjugated) was hydrolyzed. Similarly with enzyme hydrolysis, ECL increased 1.4-fold when 6-APA (nonconjugated) in a mixture of 6-APA and Ru(bpy)$_3^{+2}$ was hydrolyzed, while ECL increased 31.8-fold when Ru-APA (conjugated) was hydrolyzed. The data establishing these conclusions is found in FIG. 13 which shows the experimentally measured luminescence of (from left to right):

Ru(bpy)$_3^{+2}$ alone;
Ru(bpy)$_3^{+2}$ plus unhydrolyzed 6-APA;
Ru(bpy)$_3^{+2}$ plus NaOH-hydrolyzed 6-APA;

unhydrolyzed Ru-APA;
NaOH-hydrolyzed Ru-APA;
Ru(bpy)$_3^{+2}$ plus unhydrolyzed 6-APA;
Ru(bpy)$_3^{+2}$ plus beta-lactamase-hydrolyzed 6-APA;
unhydrolyzed Ru-APA; and
beta-lactamase-hydrolyzed APA.

This work clearly demonstrates that conjugation of the 6-APA and the electrochemiluminescent ruthenium complex result in intramolecular effects that increase the electrochemiluminescence when the beta-lactam ring is hydrolyzed. Moreover, comparison with the results described in Example 2 for the ampicillin conjugate show that hydrolysis of Ru-APA results in a much greater electrochemiluminescence signal than hydrolysis of Ru-AMP. Because the ruthenium atom is closer to the beta-lactam ring in Ru-APA than in Ru-AMP, these results indicate that there may be a critical effect of the distance between the ruthenium complex and the beta-lactam ring. Other, as-yet untested beta-lactam-Ru (bpy)$_3^{+2}$ conjugates may give an even more dramatic change in the electrochemiluminescence upon beta-lactam hydrolysis.

Figure 14:
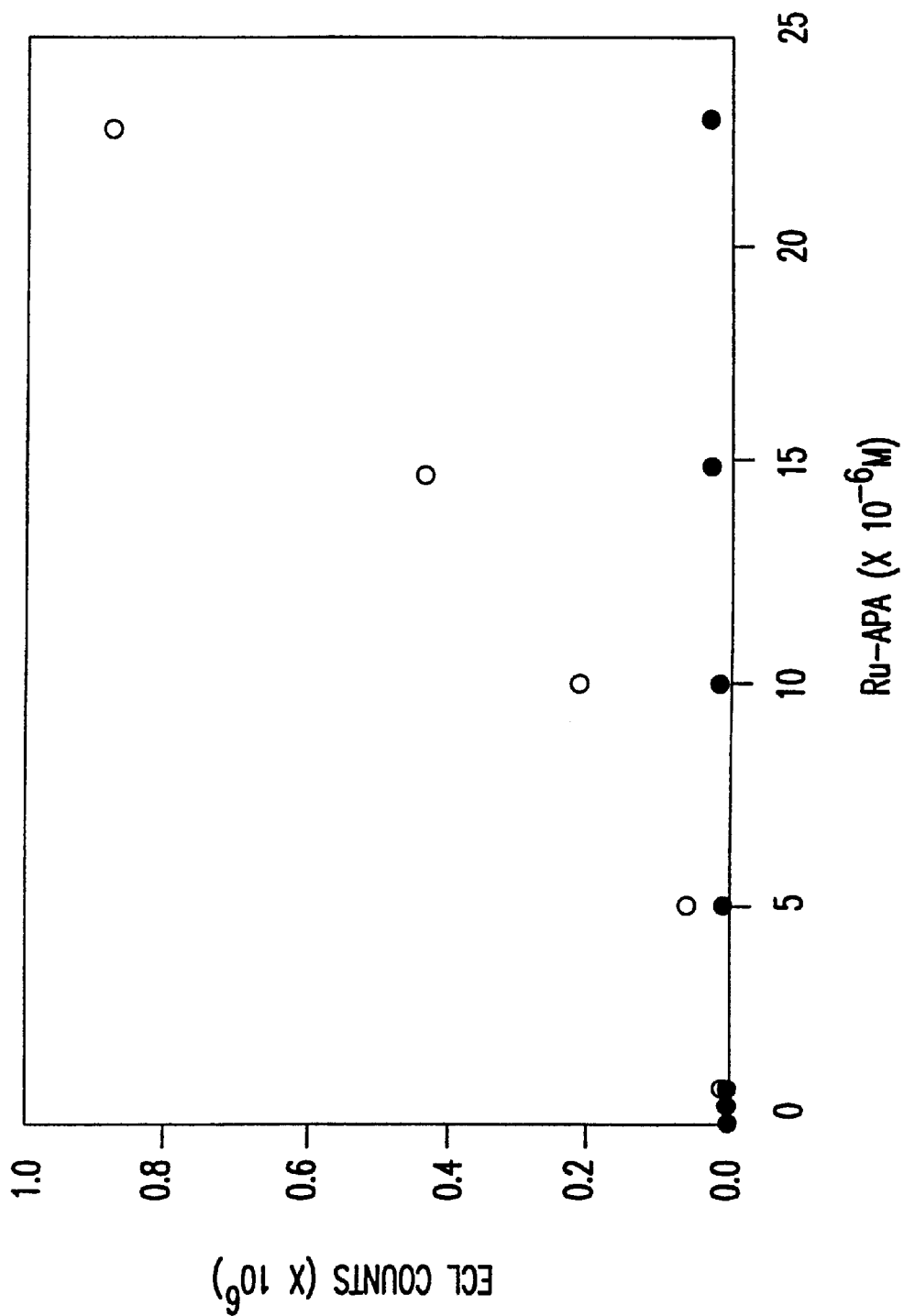
FIG. 14 shows the effect of unhydrolyzed (closed circles) and hydrolyzed (open circles) Ru-APA concentration on the measured ECL.

FIG. 14 shows that the hydrolysis of very low concentrations of Ru-APA can be detected by ECL. More specifically, FIG. 14 shows the effect of unhydrolyzed (closed circles) and hydrolyzed (open circles) Ru-APA concentration on the experimentally measured electrochemiluminescence. The lower limit of detection was found to be 50 nM (an instrument reading of −33 relative ECL counts for hydrolyzed Ru-APA versus an average of −648 relative ECL counts for unhydrolyzed Ru-APA (conjugated).) This compares favorably to the lower limit for detection of (unconjugated) APA hydrolysis which was 50 μM (in the presence of 10 μM Ru(bpy)$_3^{+2}$.

Figure 15:
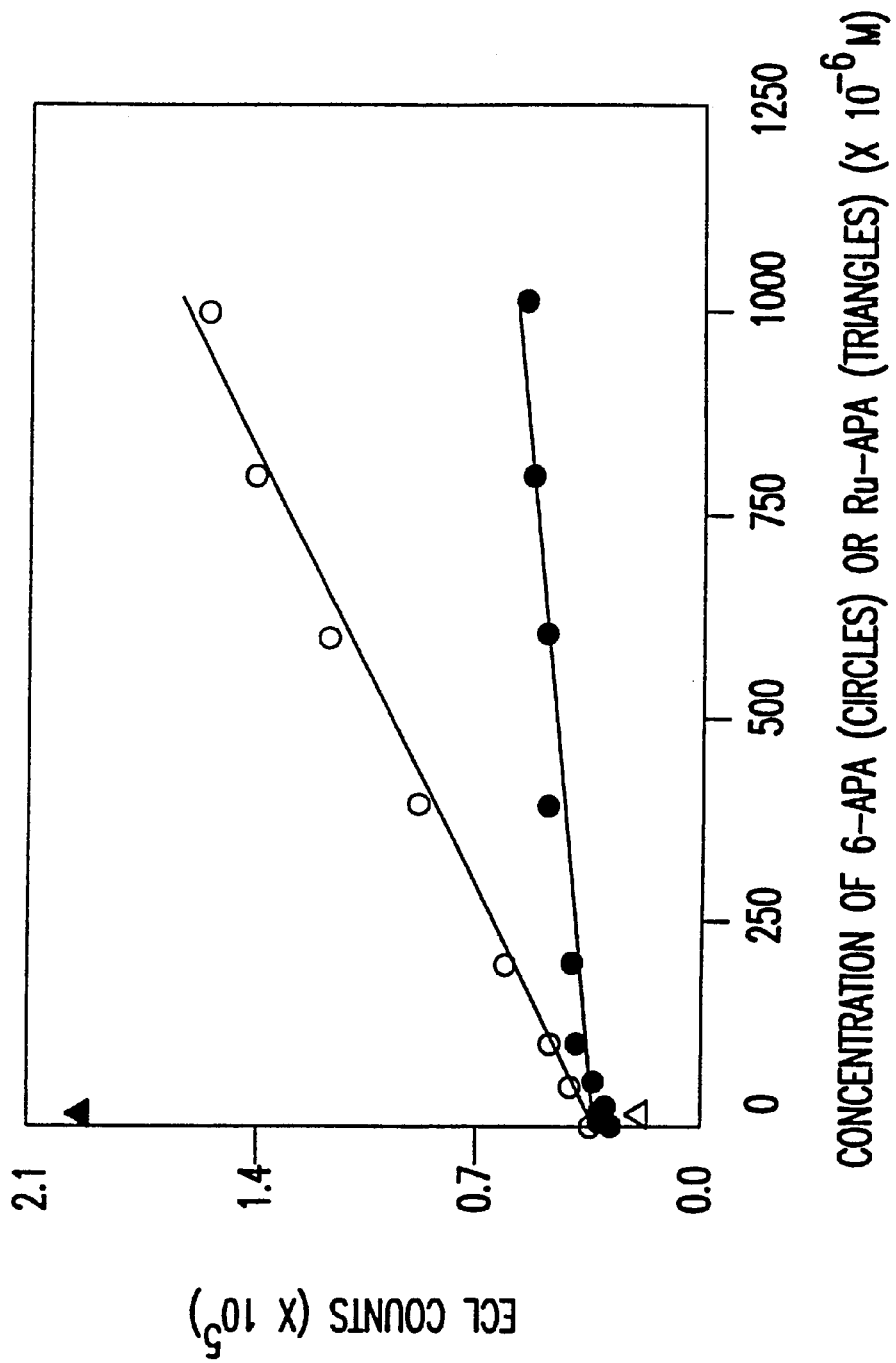
FIG. 15 shows the comparison of measured ECL for a series of different samples.

An experiment was performed to quantitate the advantage of conjugating a beta-lactam to the ECL label, Ru(bpy)$_3^{+2}$. The increase in ECL upon hydrolysis of 10 μM Ru-APA was compared to an ECL standard curve in which various concentrations of 6-APA (nonconjugated) were hydrolyzed in the presence of 10 μM Ru(bpy)$_3^{+2}$. By extrapolation of the 6-APA standard curve, the results (FIG. 15) demonstrates that the ECL change upon hydrolysis of 10 μM Ru-APA (conjugated) is equivalent to the ECL change in the hydrolysis of 1250 μM 6-APA (nonconjugated) in the presence of 10 μM Ru(bpy)$_3^{+2}$. This demonstrates that conjugation of Ru(bpy)$_3^{+2}$ and 6-APA results in a 125-fold increase in the ECL change seen during 6-APA hydrolysis. The data establishing these conclusions is found at FIG. 15 which shows a comparison of electrochemiluminescence effects of Ru-APA (conjugated) to Ru(bpy)$_3^{+2}$ plus 6-APA (unconjugated). Triangles represent the electrochemiluminescence of 10 μM unhydrolyzed (open triangles) and hydrolyzed (closed triangles) Ru-APA. Circles represent the electrochemiluminescence effects of unhydrolyzed (closed circles) and hydrolyzed (open circles) 6-APA (0–1000 μM) in the presence of 10 μM Ru(bpy)$_3^{+2}$. Extrapolation in FIG. 15 indicates the electrochemiluminescence change upon hydrolysis of 10 μM Ru-APA is equivalent to the electrochemiluminescence change upon hydrolysis of 1250 μM free 6-APA in the presence of 10 μM Ru(bpy)$_3^{+2}$.

Example 4

Preparation of Ru(bpy)$_3^{+2}$-labeled β-nicotinamide adenine cofactors (a) Theory of Oxidoreductase Enzymes and Their Use in Assays β-Nicotinamide adenine cofactors (such as NAD$^+$, NADH, NADP$^+$, NADPH) are widely used in nature by oxidoreductase enzymes as oxidants or reductants during reduction or oxidation of metabolites. Such enzymes include many dehydrogenases (lactate dehydrogenase, alcohol dehydrogenase, glucose dehydrogenase, etc.). The oxidized forms of these cofactors (NAD$^+$ or NADP$^+$) have little or no TPA-like effects in ECL. However, the reduced forms (NADH or NADPH) behave like TPA in promoting Ru(bpy)$_3^{+2}$ electrochemiluminescence (1, 2). Consequently, ECL can be used to measure the enzyme-catalyzed formation or disappearance of the reduced forms of these cofactors. Hence, substrates (glucose, ethanol, etc.) of dehydrogenases can be detected by ECL since their chemical transformations by the appropriate enzyme stoichiometrically results in oxidation or reduction of nicotinamide adenine cofactors.

Figure 16:
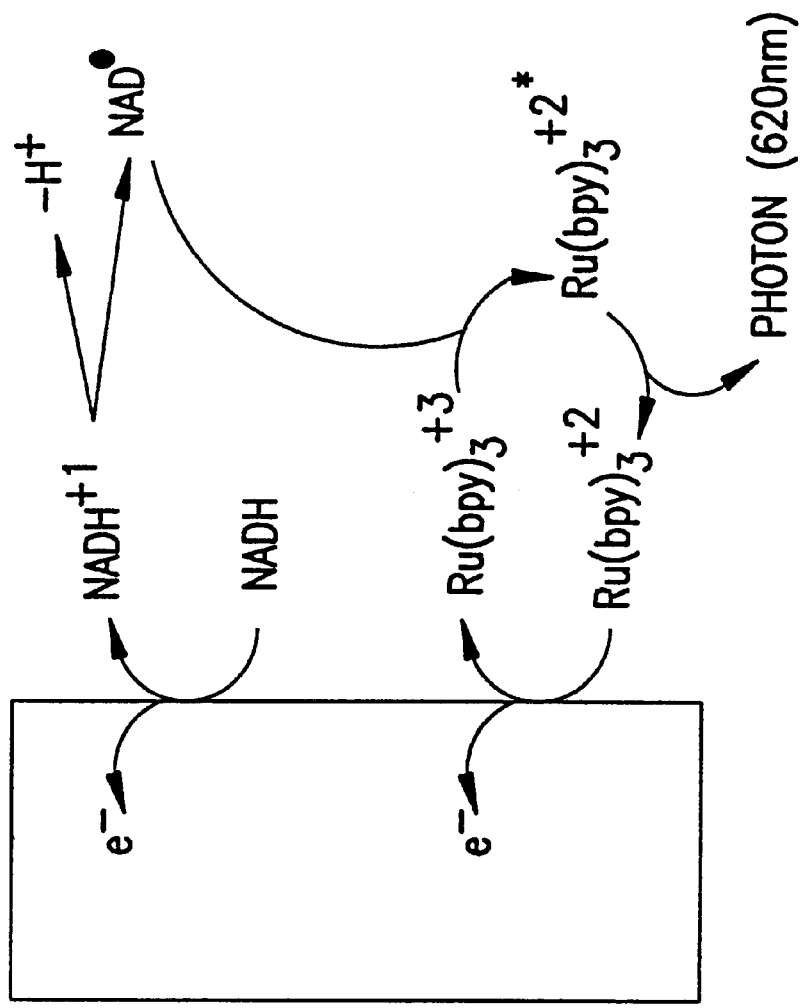
FIG. 16 shows a proposed ECL mechanism depicting reaction steps associated with the NADH-promoted ECL of $Ru(bpy)_3^{+2}$.

Reduced nicotinamide cofactors (NADH or NADPH) are not believed to be destroyed during the ECL reactions as are TPA and beta-lactams, but are instead converted to their oxidized forms (NAD$^+$ or NADP$^+$). This means that, in the presence of an appropriate dehydrogenase enzyme, nicotinamide adenine cofactors can be reused such that a single cofactor molecule that is covalently linked to an electrochemiluminescent compound can participate in multiple ECL reactions (FIG. 16). Note also in FIG. 16 that the Ru(bpy)$_3^{+2}$ is also regenerated so that it is possible for a single detectable compound comprising such a cofactor covalently linked to an electrochemiluminescent compound can possibly emit multiple photons one after another.

Nicotinamide adenine cofactors have advantages over present electrochemiluminescent techniques that use TPA. Specifically, these cofactors (i) can participate in regenerative ECL reaction mechanisms; (ii) can be used to detect and quantitate dehydrogenases and their corresponding substrates. One disadvantage is that the ECL signal (i.e., the experimentally measured luminescence) is less in an ECL reaction with NADH or NADPH than in an ECL reaction with TPA. This disadvantage could be reduced or obviated by using a conjugate of derivatives of Ru(bpy)$_3^{+2}$ and the nicotinamide adenine cofactor. As shown in the Examples above, when Ru(bpy)$_3^{+2}$ is conjugated to a chemically-transformable first compound which can act as a high energy reductant and intramolecularly donate an electron to the covalently linked electrochemiluminescent compound (such as a beta-lactam), the ECL signal generated is much greater than when the CTFC is not conjugated with the EC. Similarly, a Ru(bpy)$_3^{+2}$-nicotinamide adenine cofactor (reduced form) conjugate will also have more ECL than a nonconjugated mixture of Ru(bpy)$_3^{+2}$ and the reduced cofactor. Similarly, the difference in ECL signal between the reduced (NADH or NADPH) and oxidized forms (NAD$^+$ NADP$^+$) of the cofactors will be greater when the cofactors are covalently linked to the Ru(bpy)$_3^{+2}$ than when they are not conjugated.

Conjugates of nicotinamide adenine cofactor derivatives are known and are enzymatically functional (3,4). One such cofactor derivative, N$^6$-([6-aminohexyl]carbamoylmethyl) nicotinamide adenine dinucleotide, is commercially available (Sigma Chem. Co., St Louis, Mo.). The primary amino group of this compound can be used to couple this compound to the same Ru(bpy)$_3^{+2}$-NHS ester described above (obtainable from IGEN, Inc., Gaithersburg, Md.) by the same or similar method (FIG. 17) (3,4). Other similar coupling methods will also work. The conjugate (Ru-NAD) can be purified by HPLC in a similar manner as described for purification of Ru-AMP and Ru-APA. The four references noted above are (1) Downey, T. M. & Nieman, T. A. (1992) Anal. Chem. 64, 261–268; (2) Martin, A. F. & Nieman, T. A. (1993) Anal. Chem. Acta. 281, 475–481; (3)

Figure 17:
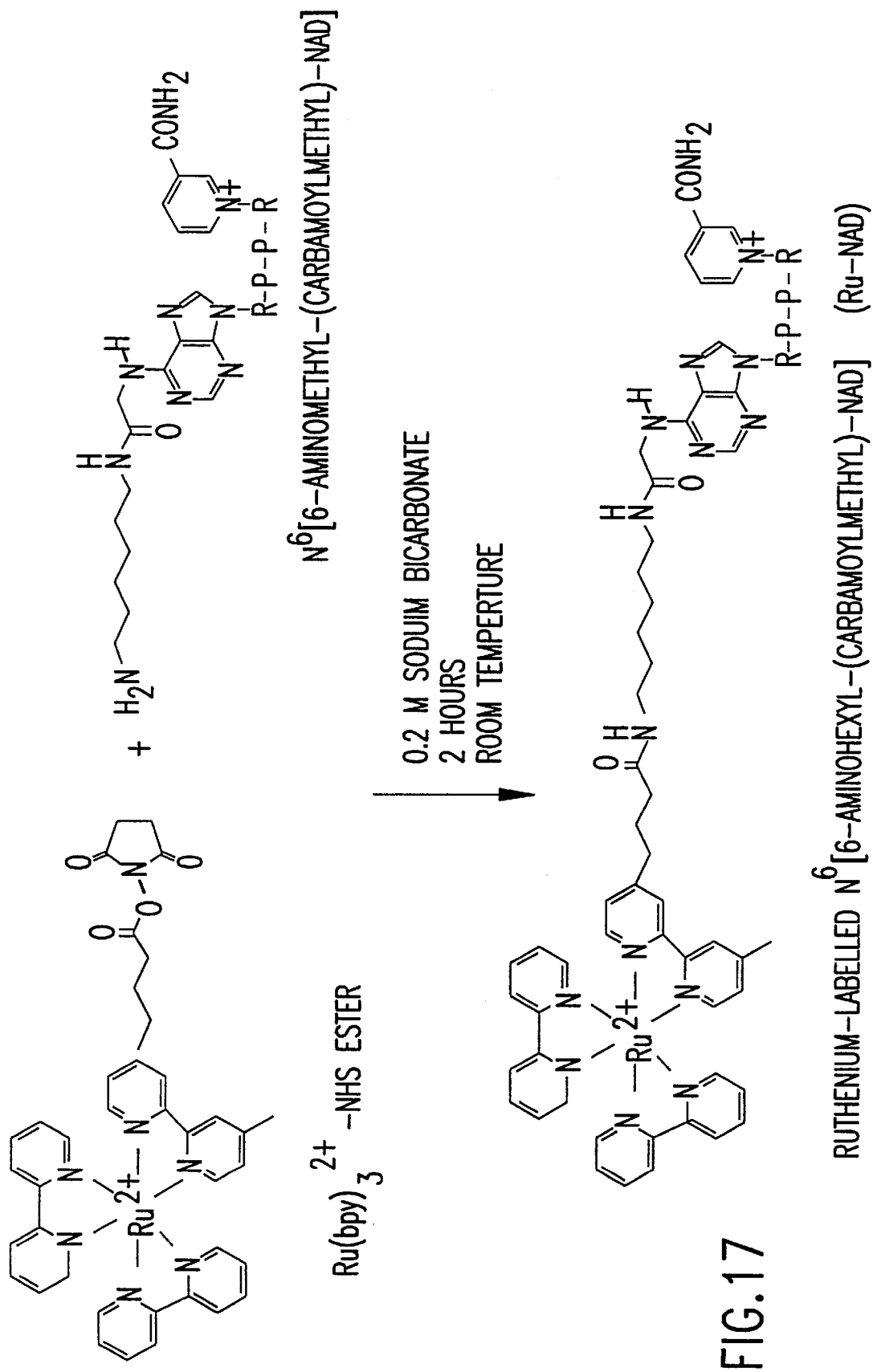
FIG. 17 shows the synthesis of Ru-NAD.

Mansson, M. -O., Larsson, P. -O., & Mosbach, K. (1982) Methods Enzym. 89, 457–468; and (4) Persson, M., Mansson, M. O., Bulow, L., Mosbach, K. (1991) Bio/Technology 9, 280–284. Each of these four references is incorporated by reference. FIG. 17 shows the preparation of Ru-NAD.

The oxidized form of Ru-NAD (Ru-NAD$^+$) can be used in enzyme assays in an ECL instrument to detect and quantitate a dehydrogenase enzyme or a substrate of a dehydrogenase (or some compound that gives rise to either). The assays will be performed according to conventional protocols (duration, temperature, pH, buffer, salt, substrate and enzyme concentrations, etc.) except that NAD$^+$ normally included will be excluded and Ru-NAD$^+$ will be used in place. The concentration of Ru-NAD$^+$ may be lower or higher than the conventional assays owing to differences in substrate specificity, solubility, cost, or other factors. Following the incubation, the mixture will be analyzed in an ECL instrument (IGEN, Inc., Gaithersburg, Md.). No additional Ru(bpy)$_3^{+2}$ will be added. Reduction of Ru-NAD$^+$ will be recognized by an increase in ECL signal over background and will indicate the presence of the relevant dehydrogenase and substrate.

Similarly, oxidation of the reduced form of Ru-NAD (Ru-NADH) can be detected by ECL. Again, conditions, and the presence of relevant enzyme and enzyme substrate will be considered and will be derived from known conditions for assays involving nonconjugated NADH. NADH will be omitted from the assay and Ru-NADH (at an appropriate concentration that may not be the conventional concentration) will be included. Following incubation, the mixture will be analyzed with an ECL instrument. Any decrease in ECL from the initial Ru-NADH signal will indicate that some Ru-NADH has been oxidized and will be evidence of the presence of the relevant enzyme or substrate.

(b) Preparation of Ruthenium-Labelled N$^6$[6-aminohexyl-(carbamoylmethyl)-NAD$^+$ To a solution containing 6.6 mg N$^6$[6-aminohexyl-(carbamoylmethyl)-NAD$^+$ (Li$^+$ salt, Sigma Chem. Co., St. Louis, Mo.) in 0.4 mL of a 1:1 mixture of acetonitrile and NaHCO$_3$ (0.2 M, pH 8.6) was added an NHS ester of Ru(bpy)$_3^{2+}$ (IGEN, Inc., Gaithersburg, Md.) in 0.2 mL of a 1:1 mixture of acetonitrile and NaHCO$_3$ (0.2 M, pH 8.6). The reaction mixture was run overnight at room temperature. The following morning, the reaction was stopped, the solvent removed, and the compound was purified by size exclusion chromatography (BioRad Bio-Gel P-2, BioRad Laboratories, Richmond, Calif.). Proton NMR showed the compound to be correct, but not completely pure. The compound (Ru-NAD) was repurified on a column of Sp-Sephadex (Pharmacia, Uppsala, Sweden), eluting with changes of increasing concentrations of trifluoroacetic acid (0, 0.05, 0.2, 0.3 M). NMR showed to compound to be pure Ru-NAD.

(c) Ru-NAD as an Enzyme Cofactor

To determine whether Ru-NAD was functional as an enzyme cofactor, a reaction involving oxidation of D-glucose-6-phosphate by glucose-6-phosphate dehydrogenase was tested. The reaction was monitored spectrophotometrically at 340 nm. This wavelength is commonly used to observe the interconversion of NAD$^+$ and NADH. A mixture of 63 $\mu$M Ru-NAD, 400 $\mu$M glucose-6-phosphate, and 22 nM enzyme in 55 mM Tris buffer, pH 7.8 containing 33 mM MgCl$_2$ was incubated at 30° C. in a cuvette. Continuous absorbance readings showed that absorbance increased over approximately 40 minutes in a fashion characteristic of enzymatic reduction of NAD$^+$. This indicated that Ru-NAD was indeed accepted as a functional cofactor by glucose-6-phosphate dehydrogenase.

(d) Effect of Enzymatic Reduction on the ECL of Ru-NAD

Ru-NAD was found to be accepted as a cofactor by the dehydrogenase, glucose-6-phosphate dehydrogenase. An experiment was performed involving oxidation of glucose-6-phosphate by this enzyme with concurrent reduction of Ru-NAD. Here, ECL measurements were made to determine if; (1) the ECL-inducing effects of NADH (but not NAD$^+$) are also present in Ru-NADH (but not Ru-NAD) and (2) if conjugation of Ru(bpy)$_3^{2+}$ with NADH causes an increase in ECL measurement sensitivity as compared to the ECL of a mixture of unconjugated Ru(bpy)$_3^{2+}$ and NADH. The results are shown below (all solutions contain the substrate, glucose-6-phosphate, solutions not containing Ru-NAD contained 1.0 $\mu$M Ru(bpy)$_3^{+2}$;

| Sample | ECL counts |
|---|---|
| 21 $\mu$M NAD$^+$ | 45,500 |
| 21 $\mu$M NAD$^+$ + enzyme | 45,200 |
| 21 $\mu$M NADH | 47,900 |
| 21 $\mu$M NADH + enzyme | 40,800 |
| 21 $\mu$M Ru-NAD | 71,700 |
| 21 $\mu$M Ru-NAD + enzyme | 132,000 |

These results show that addition of enzyme to Ru-NAD increases the ECL signal. Also the results show that, at unconjugated NAD concentrations too low for ECL effects to be seen, Ru-NAD clearly gives a large amount of ECL when enzyme is added. In conclusion, Ru-NAD behaves in the same way as free Ru(bpy)$_3^{2+}$ plus free NAD$^+$ in an ECL instrument (enzyme addition causes an increase in ECL), but Ru-NAD is much more sensitively detected. This indicated that low concentrations of dehydrogenases or their substrates can be sensitively detected by ECL of Ru-NAD$^+$ reduction or Ru-NADH oxidation.

The scope of the patent protection which the present invention is entitled to is not limited by the preceding text. Rather, the present invention is defined by the claims appended hereto and all embodiments falling thereunder.

We claim:

1. A detectable electrochemiluminescent compound comprising a first compound covalently linked to an electrochemiluminescent compound, wherein, upon exposure of the detectable compound to electrochemical energy, the first compound causes the electrochemiluminescent compound to electrochemiluminesce.

2. The detectable electrochemiluminescent compound of claim 1 wherein said first compound is a chemically-transformable compound capable of being chemically transformed upon interaction with at least one second compound.

3. The detectable electrochemiluminescent compound of claim 1 wherein said first compound is a chemically-transformable compound capable of intramolecularly donating an electron to the electrochemiluminescent compound to cause the electrochemiluminescent compound to subsequently luminesce.

4. The detectable electrochemiluminescent compound of claim 3 wherein said first compound is capable of varying its ability to effect such intramolecular donation of an electron before and after any such interaction.

5. The detectable electrochemiluminescent compound of claim 1 wherein, upon exposure of the detectable compound to electrochemical energy, the first compound intramolecularly donates an electron to the electrochemiluminescent compound to cause the electrochemiluminescent compound to luminesce.

6. The detectable electrochemiluminescent compound of claim 2 wherein the first compound is a substrate and at least one second compound is an enzyme specific to that substrate.

7. The detectable electrochemiluminescent compound of claim 1 wherein the first compound is a comediator of an enzyme catalyzed conversion of a nonconjugated substrate to a nonconjugated product.

8. An electrochemiluminescent process for monitoring chemical transformations of compounds, comprising:

(a) contacting a detectable compound as defined in claim 2 to a sample solution suspected of containing at least one second compound;

(b) exposing the detectable compound to electrochemical energy to cause electrochemiluminescence;

(c) measuring the luminescence emitted by the detectable compound; and (d) monitoring the presence of any such chemical transformations of the first compound by comparing the measured luminescence with a predetermined standard.

9. The process of claim 8 wherein the monitoring step further includes quantitatively calculating the extent to which the first compound has been chemically modified.

10. The process of claim 8 wherein the monitoring step, independent of the actual identification of any second compound, further determines whether there are any second compounds in the sample solution capable of effecting such chemical transformations in the first compound and wherein the process is repeated with a series of sample solutions in a screening fashion that is capable of selecting, based on the measured luminescence, any particular sample solution for further investigation.

11. The process of claim 8 wherein the determining step is part of a process for performing an assay for at least one particular second compound whose presence or absence is determined from the measured luminescence of step (d) and wherein a particular detectable compound corresponding to and capable of being chemically transformed by exposure to the particular second compound is used in the process.

12. The process of claim 11 wherein the determining step further includes quantitatively calculating the amount of the particular second compound.

13. The process of claim 11 wherein the first compound is a substrate and the second compound is an enzyme both specific for the first compound and capable of catalyzing the chemical transformation of the first compound upon interaction therewith.

14. A kit useful for preparing a predetermined luminescence standard comprising a plurality of test sample solutions each containing differing known amounts of a particular detectable compound as defined in claim 2, provided that each of the solutions does not contain any second compounds, and provided that each of the test sample solutions is capable of being induced to electrochemiluminesce at experimentally measured levels that are sufficiently distinct from one another so that a luminescence calibration curve can be constructed from such levels.

15. A kit useful for preparing a predetermined luminescence standard comprising:

(a) a plurality of first test solutions each containing known amounts of a particular detectable compound as defined in claim 2, provided that each of the first solutions does not contain any second compounds; and (b) a plurality of second test solutions respectively matching in total number the number of first test sample solutions, each of the second test solutions containing differing amounts of a particular second compound corresponding to and capable of effecting a chemical transformation in the particular detectable compound, provided that the set of first test solutions and the set of second test solutions are ready to be mixed, under conditions permitting any such chemical transformations to occur, pairwise with each other to form a set of third test solutions, and provided that each of the third test solutions is capable of being induced to electrochemiluminesce at experimentally measured levels that are sufficiently distinct from one another so that a luminescence calibration curve can be constructed from such levels.

16. A detectable electrochemiluminescent compound, comprising a first compound capable of reacting with a second compound, said first compound covalently linked to an electrochemiluminescent compound, wherein, upon exposure of the detectable compound to electrochemical energy, the first compound causes the electrochemiluminescent compound to electrochemiluminesce.

17. The detectable electrochemiluminescent compound of claim 1, wherein said electrochemiluminescent compound comprises at least one ruthenium-containing or osmium-containing chemical moiety.

18. The detectable electrochemiluminescent compound of claim 16, wherein said electrochemiluminescent compound comprises at least one ruthenium-containing or osmium-containing chemical moiety.

\* \* \* \* \*

UNITED STATES PATENT AND TRADEMARK OFFICE
CERTIFICATE OF CORRECTION

PATENT NO. : 6,165,708
DATED : December 26, 2000
INVENTOR(S) : Liang et al.

It is certified that error appears in the above-identified patent and that said Letters Patent is hereby corrected as shown below:

Column 18,
Line 61, change "luminesce" to -- electrochemiluminesce --.

Column 19,
Lines 21 and 25, change "luminescence" to -- electrochemiluminescence --.
Line 36, change "luminescence" to -- electrochemiluminescence --.
Line 41, change "luminescence" to -- electrochemiluminescence --.

Column 20,
Lines 3 and 11, change "luminescence" to -- electrochemiluminescence --.
Lines 13 and 32, change "luminescence" to -- electrochemiluminescence --.

Signed and Sealed this

Nineteenth Day of February, 2002

Attest:

Attesting Officer

JAMES E. ROGAN
Director of the United States Patent and Trademark Office